(12) United States Patent
Brenner et al.

(10) Patent No.: US 8,014,953 B2
(45) Date of Patent: Sep. 6, 2011

(54) RNA SURVEILLANCE AMONG CURATED PROTEINS

(75) Inventors: Steven E. Brenner, Berkeley, CA (US); Richard E. Green, Berkeley, CA (US); R. Tyler Hillman, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1843 days.

(21) Appl. No.: 10/637,482

(22) Filed: Aug. 8, 2003

(65) Prior Publication Data

US 2005/0032071 A1 Feb. 10, 2005

(51) Int. Cl.
*G01N 33/48* (2006.01)
(52) U.S. Cl. .......................................... 702/19
(58) Field of Classification Search ............... 702/19
See application file for complete search history.

(56) References Cited

U.S. PATENT DOCUMENTS 7,149,631 B2 * 12/2006 Brenner et al. ................. 702/19

OTHER PUBLICATIONS

Nagy et al. TIBS (1998) vol. 23, pp. 198-199).*
Green et al. (Bioinformatics (Jul. 2003) vol. 19, Suppl. 1, pp. i118-i121).*
Pruitt et al. "RefSeq and Locus Link: NCBI gene-centered resources" Nucleic Acids Research, vol. 29, (Jan. 1, 2001), pp. 137-140.*

* cited by examiner

*Primary Examiner* — Jerry Lin
(74) *Attorney, Agent, or Firm* — Richard Aron Osman

(57) ABSTRACT

Computational methods for systematically characterizing putative protein isoforms as apparent targets of nonsense-mediated decay (NMD) comprise: (a) identifying a dataset of target putative protein isoform sequences for characterization; (b) identifying from an mRNA dataset corresponding mRNA sequences representing transcripts encoding the protein isoforms; (c) determining corresponding gene intron-exon structures by mapping the mRNA sequences to corresponding genomic sequences; and (d) determining if the transcripts are apparent targets of NMD. Methods for regulating the expression of a gene encoding a protein isoform characterized as an apparent target of NMD comprise biasing expression of the isoform by modulating transcript splicing or modulating NMD activity.

8 Claims, No Drawings

RNA SURVEILLANCE AMONG CURATED PROTEINS

This invention was made with Government support under Grant Nos. 732-HG000747 and 1-K22-HG00056 awarded by the National Institutes of Health. The Government has certain rights in this invention.

INTRODUCTION

1. Field of the Invention

The field of the invention is computational and molecular methods relating to gene regulation by alternative splicing and nonsense-mediated decay.

2. Background of the Invention

Alternative splicing is an intensely studied cellular phenomenon whereby cells can produce multiple versions of many of the genes encoded in their genomes. Current estimates are that more than one-half of all human genes undergo alternative splicing. We recently disclosed that many of these alternative transcripts are targets of a degradation pathway known as nonsense-mediated mRNA decay (NMD) (ref. 1, and U.S. patent application Ser. No. 10/159,997). Here we disclose our development of a computational protocol for identifying likely NMD targeted isoforms from amongst the well-characterized alternative isoforms in protein databases. For example, applying our protocol to the Swiss-Prot database, we characterized 177 human alternative isoforms as targets of NMD. Amongst these are isoforms of Calpain-10, CLK1, CLK2, CLK3, and LARD/TNFRSF12. We also disclose a protocol for characterizing polymorphisms as generative of NMD targeted isoforms.

SUMMARY OF THE INVENTION

We extend, adapt and apply our prior invention to analysis of protein isoform datasets for putative isoforms that are encoded by transcripts that are targets of NMD. The invention provides methods for characterizing purported protein isoforms, and for using the resultant characterization to guide use of the proteins, and particularly to modulate predetermined isoform expression. The invention provides characterization protocols, as well as output databases comprising lists of isoforms subject to NMD. The invention also provides protein-specific methods, such as NMD-based methods for regulating the expression of each identified protein. The invention includes subsets of the identified protein isoforms, particularly subsets which exclude any isoforms previously suggested by others to be NMD targets.

In particular embodiments, the invention provides computational methods for characterizing a putative protein isoform as an apparent target of NMD, comprising the steps of:

(a) identifying a target putative protein isoform sequence for characterization;

(b) identifying one or more corresponding mRNA sequences representing a transcript encoding the protein isoform;

(c) determining corresponding gene intron-exon structure by mapping the mRNA sequences to one or more corresponding genomic sequences;

(d) determining if the transcript is an apparent target of NMD.

In particular embodiments, the invention provides computational methods for systematically characterizing putative protein isoforms as apparent targets of NMD, comprising the steps of:

(a) identifying a dataset of target putative protein isoform sequences for characterization;

(b) identifying from an mRNA dataset corresponding mRNA sequences representing transcripts encoding the protein isoforms;

(c) determining corresponding gene intron-exon structures by mapping the mRNA sequences to corresponding genomic sequences; and (d) determining if the transcripts are apparent targets of NMD.

In particular embodiments, the invention provides computational methods for systematically characterizing putative protein isoforms as apparent targets of NMD, comprising the steps of:

(a) identifying a dataset of target putative protein isoform sequences for characterization;

(b) identifying corresponding gene intron-exon structure by mapping corresponding mRNA sequences of an mRNA sequence dataset to genomic sequences of a genomic DNA sequence dataset;

(c) screening the isoform dataset for a subset of isoforms encoded by transcripts comprising alternate splices which introduce a stop codon more than 50 bp upstream of the final exon-exon splice junction; and (d) classifying the subset isoforms as being encoded by transcripts comprising premature stop codons and as targets of NMD.

In particular embodiments, the invention further comprises the step of correlating the isoforms with relative expression in different cell types, particularly cancer cells and non-cancer cells.

The invention also provides methods for regulating the expression of a gene encoding a protein isoform of Table 1, said method comprising the step of biasing expression of the isoform by modulating transcript splicing or modulating NMD activity, particularly wherein the isoform expression is biased with an inhibitor selected from the group consisting of: an aminoglycoside drug like gentamycin which causes translational readthrough; a dominant negative hUpf1, expression of which inhibits NMD; an hUpf1-targeted RNAi which inhibits NMD; an antisense exon or a specific splicing factor, expression of which inhibits NMD; and a splice-selection altering amount of dimethyl sulfoxide which inhibits NMD.

The invention also provides datasets of putative protein isoforms characterized as apparent targets of NMD by a subject method, particularly wherein the datasets comprise a subset of the isoforms of Table 1, particularly isoforms of Calpain-10, CLK1, CLK2, CLK3, and LARD/TNFRSF12. These datasets may be in any convenient form, including stored in or on an electronic medium.

DETAILED DESCRIPTION OF PARTICULAR EMBODIMENTS OF THE INVENTION

The following descriptions of particular embodiments and examples are offered by way of illustration and not by way of limitation We disclose that about 10% of the alternatively spliced entries in the SWIS-PROT protein database have a premature termination codon, making them candidates for nonsense-mediated decay. Our findings indicate that many purported alternatively spliced protein forms naturally exist in lower abundance than previously thought, and in many cases NMD reduces their abundance to undetectable and insignificant levels. We provide a list of several hundred such purported isoforms, and detailed exemplary analyses of three of them.

Our findings provide an unappreciated approach—selective NMD targeting—for regulating the expression of these proteins.

I. Computational method for identifying likely NMD-targets in Swiss-Prot and other highly curated databases. Many curated biological sequence databases support annotation of alternative splicing. Because the cloning and characterization of many genes predates our current understanding of NMD in vertebrates, many of the alternative isoforms described in these databases are unrecognized targets of NMD. A series of recent experiments from several labs has outlined the mechanistic details of vertebrate NMD. The model of NMD demonstrated by these experiments combined with the following computational analysis of mRNA transcripts allows us to predict which isoforms are likely targets for NMD. Knowing that a transcript is degraded by NMD is critically important for understanding its function. It is largely assumed that genes that are expressed as mRNA go on to be expressed as protein. However, when NMD intervenes, little or no protein product is made and the gene is effectively off.

Our method for discovering which alternative isoforms are likely NMD targets from a database of isoform sequences is as follows. First, we identify the transcript sequence of each isoform from a relevant database. This database may or may not be separate from the database being screened. Then, using complete genomic sequence, we use SPIDEY or a similar transcript-to-genome alignment program to determine where introns have been spliced out of each transcript. A comparison of the position of the termination codon to the position of introns then reveals if the transcript is likely to be recognized and degraded by NMD. If the termination codon is more than 50 nucleotides upstream of the final intron position, then the transcript is an apparent target of NMD.

II. Identification of 177 human alternative isoforms from Swiss-Prot that are likely targets of NMD including Calpain-10, CLK1, CLK2, and CLK3, and LARD/TNFRSF12. Using the above protocol, we screened the human alternative isoforms of the Swiss-Prot database. This screen identified 130 alternatively spliced genes that generate 177 isoform transcripts that are likely targets of NMD.

Further investigation of several of these revealed that they are bona-fide targets of NMD. Calpain-10, for example, is a ubiquitously expressed protease that is alternatively spliced to produce eight isoforms. A literature report describes four of these isoforms as "less abundant". These same four isoforms were identified in our screen to be likely NMD targets.

We also identified as likely NMD targets isoforms of the human splice regulators CLK1, CLK2, and CLK3. CLKs, also known as LAMMER kinases, have been shown to regulate alternative splicing by phosphorylating and thereby activating SR proteins. Alignment of the CLK1, CLK2, and CLK3 human paralogs reveals that all three share a conserved splicing pattern comprised of a full-length isoform and a shorter, premature termination codon (PTC)-containing isoform generated by skipping exon 4. EST data show this alternative splicing pattern is evolutionarily conserved through mice and sea squirts. A prior investigation of the relative expression of the CLK1 splice variants shows that the PTC-containing isoform is "up-regulated" relative to the non-PTC isoform following treatment with cycloheximide, a potent NMD inhibitor. While this up-regulation was previously attributed to the cellular stress response, our results indicate alleviation of NMD is responsible for the higher abundance of the PTC form.

Intriguingly, CLK1 has also been shown to affect its own splicing. The presence of high levels of CLK1 protein favors generation of the PTC-containing mRNA isoform that we expect to be targeted by NMD. This may set up an autoregulatory feedback loop analogous to that seen for SC35, which auto-regulates its own expression via alternative splicing-induced NMD.

We also identified several isoforms of the death domain-containing receptor TNFRSF12/LARD/DR3/Apo3 as likely NMD targets. Death domain-containing receptor proteins regulate the balance between lymphocyte proliferation and apoptosis. Resting lymphocytes express several short TNFRSF12 isoforms of unclear function. In contrast, activated lymphocytes produce only the full-length TNFRSF12, which induces apoptosis. We found that the five short TNFRSF12 mRNA isoforms expressed in resting lymphocytes all had PTCs. This precise correlation between mRNA isoform expression and NMD-candidacy indicates that the short variants are simply degraded, while the full-length version is the only one translated normally to yield protein. Alternative splicing could thus act as a switch, regulating whether protein is expressed and thus whether the cell undergoes apoptosis.

III. Computational protocol for screening polymorphism libraries to detect NMD-targeted polymorphisms. There are several large public and proprietary databases of naturally occurring human single-nucleotide polymorphisms (SNPs). SNPs have been used for a variety of purposes. Perhaps the most common use of SNP data is in disease-linkage studies. When a specific SNP is associated with a specific disease, it can give valuable clues to the role of the gene in which the SNP occurs. Using our protocol for determining gene structures, we can make the additional assessment of whether any given SNP will likely generate an NMD-candidate isoform. In these cases, disease pathology will likely be due to haploinsufficiency rather than gain-of-function.

IV. Control of protein expression by the manipulation of splicing factors. We demonstrate that genes can be generally and predictably engineered to undergo alternative splicing, so that multiple mRNA isoforms are generated. Engineered alternative splicing can be regulated in any of the ways that alternative splicing is regulated in vivo: addition or subtraction of known alternative splicing factors, changing concentration of basal splicing factors, etc. One or more of the isoforms can be engineered to contain premature termination codons causing these mRNAs to be selectively degraded. In this way, under prescribed conditions, engineered genes can be tightly regulated. Accordingly, the novel isoforms disclosed herein provide myriad reagents, including sites, splice junctions and splice environments, with pre-determinable effects on target gene expression regulation. While precise effects are best confirmed empirically, native expression patterns of the natural target gene provide preliminary guidance for predetermining heterologous expression regulation. A particular advantage of this post-transcriptional regulation is that it can make use of endogenous splicing factors to control expression, making the method particularly well-suited for in vivo applications. Hence, this method is useful for studying the function of specific genes and proteins in cell culture, and for generating transgenic animals in which expression of exogenous genetic material is limited to certain cell types based on their splicing environment.

Accordingly, the invention provides engineering target genes to undergo alternative splicing, so that multiple mRNA isoforms, including one or more NMD-targeted isoforms, are generated, and thereby providing predetermined NMD-mediated, postranscriptional expression regulation of the gene. In a particular embodiment, the invention provides a method for regulating gene expression comprising the steps of:

genetically engineering in a target gene a change in the native pattern of splice junctions to provide at least a predetermined first, non-natural NMD-targeted splice form and a predetermined second, non-NMD-targeted splice form, wherein expression of the gene is regulated by the relative expression of the first and second splice forms; and optionally, detecting or inferring the relative expression of the first and second splice forms; and optionally, detecting or inferring a change in expression of corresponding protein isoforms.

Protocols for manipulating splicing and/or NMD are known in the art. For example, aminoglycoside drugs, like gentamicin, cause translational readthrough, and therefore inhibit NMD (e.g. Mankin and Liebman, Nat Genet. 1999 September; 23(1):8-10; Burke and Mogg, Nucleic Acids Res. 1985 Sep. 11; 13(17):6265-72); expression of a dominant negative version of hUpf1 inhibits NMD (e.g. Sun et al., Proc Natl Acad Sci USA. 1998 Aug. 18; 95(17):10009-14); RNAi directed against hUpf1 inhibits NMD (e.g. Mendell et al., Science 2002 Oct. 11; 298(5592):419-22); expressing antisense exons can prevent expression of NMD-targeted isoforms (e.g. Mann et al., Proc Natl Acad Sci USA. 2001 Jan. 2; 98(1):42-7); expressing specific splicing factors can prevent expression of NMD-targeted isoforms (e.g. Caceres and Kornblihtt, Trends in Genetics 2002 Apr. 18(4): 186-193); and chemical reagents like DMSO can prevent expression of NMD-targeted isoforms (e.g. Bolduc et al., J Biol Chem. 2001 May 18; 276(20):17597-602)

V. NMD targeted isoforms in diseased cells. The invention provides for the application of any of the foregoing experimental or computational methods in the diagnosis of disease states, such as cancer, and in the development of diagnoses and therapies based on NMD-mediated gene expression regulation.

EXAMPLES

Alternative pre-mRNA splicing endows genes with the potential to produce a menagerie of protein products. We recently found that 35% of reliable EST-inferred human alternative mRNA isoforms contain premature-termination codons (PTCs), rendering them candidate targets of a surveillance pathway known as nonsense-mediated mRNA decay (NMD) (1). This finding indicates that many alternative mRNA isoforms are not translated into functional protein but are instead targeted for degradation. Because the cloning and characterization of many genes predates an appreciation of the pervasiveness of NMD, we hypothesized that curated databases may inadvertently contain isoforms that are NMD targets. Here we report that 9.6% of the alternatively spliced human entries in SWISS-PROT that were amenable to analysis have at least one PTC-containing splice variant, making them apparent targets of NMD (Table 1).

We assembled 4556 human protein isoform sequences from 1636 alternatively-spliced human entries in the SWISS-PROT database v.41(2). We next located corresponding mRNA sequences in the REFSEQ and GENBANK bioinformatics databases and determined gene structures using SPIDEY(3) and the NCBI human genome build 30. We discarded SWISS-PROT isoform sequences for which we could not locate the corresponding mRNA sequence or assemble a suitable SPIDEY alignment. The "50-nucleotide rule" for PTCs and NAND (ref. 4 and references therein) was checked for each mRNA by comparing the position of the termination codon relative to the introns (Example Supplement 1). Of the 2523 isoform sequences from 1348 SWISS-PROT entries that passed quality filters, 177 splice variant isoforms (7.0%) from 130 entries (9.6%) were found to contain a PTC.

For several of these genes, experimental reports include data consistent with NMD action, though this possibility has been almost universally overlooked. For example, literature reports regarding Calpain-10 describe isoform abundances that correlate perfectly with our NMD prediction (Example Supplement 2). Horikawa et al. describe four of Calpain-10's eight splice variants as being expressed in "low abundance." (5) It is these same four isoforms that were found to contain PTCs, implicating NMD as the culprit behind the experimental observation.

Alternative isoforms of human CLK1, CLK2, and CLK3 were also identified in our analysis as containing PTCs. All three share a conserved splicing pattern comprised of a full-length isoform and a shorter, PTC-containing isoform generated by skipping exon 4(6). EST data show this alternative splicing pattern is evolutionarily conserved through mice and sea squirts (Example Supplement 3). A prior investigation of the relative expression of the CLK1 splice variants shows that the PTC-containing isoform is "up-regulated" relative to the non-PTC isoform following treatment with cycloheximide, a potent NMD inhibitor (7). Menegay et al. attributed this up-regulation to the cellular stress response (7); our results indicate alleviation of NMD is responsible.

CLKs are alternative splicing regulators and CLK1 has also been shown to affect its own splicing (8). The presence of high levels of CLK1 protein favors generation of the PTC-containing isoform creating a feedback loop analogous to that of SC35 (9), which auto-regulates its own expression via alternative splicing-induced NMD.

Literature reports describing the expression of TNFRSF12/LARD/DR3/Apo3 isoforms contain data consistent with NMD-associated regulation. Our analysis found six TNFRSF12 protein isoforms with PTCs. Prior to lymphocyte activation, only those isoforms that we found to contain PTCs are expressed (10). Following PHA-mediated lymphocyte activation, expression of these isoforms ceases in favor of the major, full-length isoform (10). This shift in splicing hints that alternative splicing-induced NMD may play a role in regulating lymphocyte apoptosis (Example Supplement 4). Prior to lymphocyte activation, the regulated splicing of unproductive isoforms, degraded by NMD, would hold in abeyance apoptosis which is induced by splicing the productive isoform.

Example Supplement 1

Methods (a) Extraction and assembly of alternatively spliced human protein isoforms from SWISS-PROT v41. We analyzed each of the 2292 SWISS-PROT human entries containing a VARSPLIC line in its feature table. VARSPLIC line information was used to assemble protein isoform sequence for 4556 isoforms from 1636 SWISS-PROT entries. 656 entries could not be analyzed due to ambiguous VARSPLIC annotation.

(b) Identification of corresponding mRNA/cDNA sequences. Although SWISS-PROT contains cross-references to mRNA/cDNA sequences for major protein isoforms, many alternative isoforms are not cross-referenced. To find the correct cDNA/mRNA isoform sequence for each SWISS-PROT protein isoform, we used BLAST version 2.2.4 to align each protein isoform sequence to translated mRNA/cDNA sequences from the REFSEQ and GENBANK bioinformatics databases of Mar. 22, 2003. In these alignments, >99% identity over the full length of the SWISS-PROT isoform was required. In cases of multiple matches, we selected 100% identical matches over 99% identical matches and REFSEQ matches over GENBANK matches. For SWISS-PROT isoforms matching multiple entries from the same database at the same percent identity, the match associated with the longest mRNA sequence was chosen. After applying these rules, 2787 alternatively spliced human Swiss-Prot protein isoforms were associated with a corresponding cDNA/mRNA sequences from either REFSEQ or GENBANK.

(c) Retrieving coding sequences and genomic loci. We used LOCUSLINK bioinformatics database to map each cDNA/mRNA sequence to the correct human genomic contig sequence from the NCBI human genome build 30. The CDS feature of each REFSEQ or GENBANK bioinformatics database record was used to identify the location of the termination codon.

(d) Assessing NMD candidacy. The SPIDEY mRNA to genomic alignment program was used to determine the location of introns for each cDNA/mRNA isoform sequence. SPIDEY takes as input a cDNA/mRNA sequence and the corresponding genomic sequence and generates an alignment that reveals the location of introns. We compared the intron positions to the position of the termination codon for each cDNA/mRNA isoform sequence. If the termination codon was found to be more than 50 nucleotides upstream of the final intron, it was deemed a premature-termination codon and the transcript deemed an apparent target for NMD. This was the case for 7.0% of the isoforms (177 of 2523) from 9.6% of the SWISS-PROT entries (130 of 1348).

Example Supplement 2

Expression levels of Calpain-10 isoforms are consistent with NMD prediction. Calpain-10 (Q9HC93), a ubiquitously expressed protease, is alternatively spliced to produce eight isoforms. An initial report from Horikawa and co-workers showed that several of the isoforms are expressed in low abundance. This set of isoforms correlates perfectly with the set that we determined to be NMD-candidates. This study also reported that a SNP in Calpain-10 is strongly linked to susceptibility to Type-II diabetes in several populations. This mutation lies in intronic sequence and may affect the alternative splicing of Calpain-10.

Example Supplement 3

Splicing to generate premature termination codon is evolutionarily conserved in CLKs. The cdc-like kinases (CLKs) control alternative splicing by phosphorylating SR-proteins. CLKs are alternatively spliced, themselves, in a pattern that is conserved from human through mouse and sea-squirt.

(a) Conservation across three human paralogs. Our screen of Swiss-Prot revealed that human CLK1, CLK2, and CLK3 generate premature termination codon (PTC) containing isoforms. Using SPIDEY, GFF2PS, and custom scripts, we generated gene structures that show both the full-length isoforms and the PTC containing isoform. The splicing pattern that generates the putative NMD target isoforms, skipping exon 4, is conserved in each. We also generated global alignments between corresponding exons and introns using ALIGN. The introns flanking the alternative exon are amongst the most conserved.

(b) Conservation across orthologs in human, mouse, and sea-squirt. CLKs were identified in mouse through existing annotation and in the predicted genes of Ciona Intestinalis (sea-squirt) through HMMER search using an HMM constructed with annotated CLKs from a variety of organisms. Pairwise alignment revealed the sea-squirt CLK to be most similar to CLK2. We then identified ESTs from dbEST corresponding to the three mouse CLKs and to the sea-squirt CLK. Analysis of these ESTs revealed that the PTC-generating alternative splicing pattern was conserved in each. Corresponding exons and introns were also aligned as before. However, the human CLK2 gene has 13 exons whereas sea-squirt CLK gene has 11. To ensure that we aligned homologous regions, we generated clustalw and t_coffee multiple sequence alignments of annotated CLKs from several organisms and used these alignments to guide our exon and intron alignments. This analysis clearly indicated a single extra intron in sea squirt relative to human and three extra introns in human relative to sea-squirt. As in the paralog comparison, a high degree of conservation is present in the introns flanking the alternative exon.

Example Supplement 4

TNFRSF12/LARD/DR3/Apo3 Splicing Pattern and Expression Levels. TNFRSF12 is a death domain-containing member of the nerve growth factor receptor (NGFR) family of proteins that is found almost exclusively in lymphocytes. The term "death domain" refers to a conserved intracellular region found in receptors like Fas and TNFR-1 that is capable of inducing apoptosis while in the presence of a particular ligand (in this case, FasL and TNF1 respectively). Death domain-containing receptors play a crucial role in maintaining the balance between lymphocyte proliferation and apoptosis in vivo. TNFRSF12 is alternatively spliced to produce at least 11 isoforms, though only the major splice variant (isoform 1) contains the death domain and is capable of inducing apoptosis. Six TNFRSF12 isoforms were found in our analysis of SWISS-PROT to contain PTCs, rendering them potential targets of (NMD. The splicing distribution of TNFRSF12 isoforms has been shown to change upon lymphocyte activation, indicating alternative splicing may be a control point regulating lymphocyte proliferation.

(a) Screaton et al. (10) showed that, prior to lymphocyte activation, only PTC-containing TNFRSF12 isoforms are expressed (isoforms 2, 3, 4, and 5). Primary blood lymphocytes treated with an activating agent were found to instead express the major, apoptosis-inducing splice variant (isoform 1) almost exclusively. The correlation between PTC-containing isoform expression and lymphocyte activation indicates alternative splicing-induced NMD plays a role in regulating lymphocyte proliferation. By expressing only PTC-containing isoforms prior to activation, programmed cell death would be held in abeyance. Once activated, lymphocytes could alter splicing patterns to favor expression of full-length TNFRSF12 isoform 1, inducing apoptosis.

(b) TNFRSF12 isoforms 2, 3, 4, and 5 were found in our analysis of SWISS-PROT to contain premature termination codons (PTCs), rendering them apparent targets of NMD.

PARENTHETICAL REFERENCES

1. Lewis, B. P., Green, R. E. & Brenner, S. E. Evidence for the widespread coupling of alternative splicing and nonsense-mediated mRNA decay in humans. Proc Natl Acad Sci USA 100, 189-92 (2003).
2. Boeckmann, B. et al. The SWISS-PROT protein knowledgebase and its supplement TrEMBL in 2003. *Nucleic Acids Res* 31, 365-70 (2003).
3. Wheelan, S. J., Church, D. M. & Ostell, J. M. Spidey: a tool for mRNA-to-genomic alignments. *Genome Res* 11, 1952-7 (2001).

4. Maquat, L. E. Nonsense-mediated mRNA decay. *Curr Biol* 12, R 196-7 (2002).
5. Horikawa, Y. et al. Genetic variation in the gene encoding Calpain-10 is associated with type 2 diabetes mellitus. *Nat Genet* 26, 163-75 (2000).
6. Hanes, J., von der Kammer, H., Klaudiny, J. & Scheit, K. H. Characterization by cDNA cloning of two new human protein kinases. Evidence by sequence comparison of a new family of mammalian protein kinases. *J Mol Biol* 244, 665-72 (1994).
7. Menegay, H. J., Myers, M. P., Moeslein, F. M. & Landreth, G. E. Biochemical characterization and localization of the dual specificity kinase CLK1. *J Cell Sci* 113 (Pt 18),
8. Duncan, P. I., Stojdl, D. F., Marius, R. M. & Bell, J. C. In vivo regulation of alternative pre-mRNA splicing by the Clk1 protein kinase. *Mol Cell Biol* 17, 5996-6001 (1997).
9. Sureau, A., Gattoni, R., Dooghe, Y., Stevenin, J. & Soret, J. SC35 autoregulates its expression by promoting splicing events that destabilize its mRNAs. *Embo J* 20, 1785-96 (2001).
10. Screaton, G. R. et al. LARD: a new lymphoid-specific death domain containing receptor regulated by alternative pre-mRNA splicing. *Proc Natl Acad Sci USA* 94, 4615-9 (1997).

All publications and patent applications cited in this specification and all references cited therein are herein incorporated by reference as if each individual publication or patent application or reference were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

SWISS-PROT Protein isoforms characterized as targets of NMD.

| ISOFORM NAME | ACCESSION | PROTEIN DESCRIPTION | ISOFORM NAME | ACCESSION | PROTEIN DESCRIPTION |
|---|---|---|---|---|---|
| 3BP2_HUMAN ISOFORM SHORT | P78314 | SH3 domain-binding protein 2 | HFE_HUMAN MAJOR ISOFORM | Q9HC68 | Hereditary hemochromatosis protein precursor |
| 5H4_HUMAN MAJOR ISOFORM | Q13639 | 5-hydroxytryptamine 4 receptor | I17S_HUMAN ISOFORM 2 | Q9NRM6 | Interleukin-17B receptor precursor |
| A1A1_HUMAN ISOFORM SHORT | P05023 | Sodium/potassium-transporting ATPase alpha-1 chain precursor | ICE2_HUMAN ISOFORM 1CH-1S | P42575 | Caspase-2 precursor |
| ABCD_HUMAN ISOFORM 2 | Q9NSE7 | Putative ATP-binding cassette transporter C13 | ICE8_HUMAN ISOFORM 7 | Q9C0K4 | Caspase-8 precursor |
| ABCD_HUMAN ISOFORM 3 | Q9NSE7 | Putative ATP-binding cassette transporter C13 | ICEA_HUMAN ISOFORM B | Q92851 | Caspase-10 precursor |
| AD11_HUMAN ISOFORM SHORT | O75078 | ADAM 11 precursor | ICEA_HUMAN ISOFORM C | Q92851 | Caspase-10 precursor |
| AD12_HUMAN MAJOR ISOFORM | O43184 | ADAM 12 precursor | ILF1_HUMAN ISOFORM 2 | Q01167 | Interleukin enhancer-binding factor 1 |
| AD22_HUMAN ISOFORM 2 | Q9P0K1 | ADAM 22 precursor | IRF7_HUMAN ISOFORM C | Q92985 | Interferon regulatory factor 7 |
| AKP1_HUMAN ISOFORM 2 | Q92667 | A kinase anchor protein 1 mitochondrial precursor | IRL1_HUMAN ISOFORM C | Q01638 | Interleukin 1 receptor-like 1 precursor |
| ANPB_HUMAN ISOFORM SHORT | P20594 | Atrial natriuretic peptide receptor B precursor | ITP1_HUMAN MAJOR ISOFORM | O14713 | Integrin beta-1 binding protein 1 |
| AS13_HUMAN MAJOR ISOFORM | Q8WXK3 | Ankyrin repeat and SOCS box containing protein 13 | ITP1_HUMAN ISOFORM 2 | O14713 | Integrin beta-1 binding protein 1 |
| AS13_HUMAN ISOFORM 2 | Q8WXK3 | Ankyrin repeat and SOCS box containing protein 13 | KC11_HUMAN ISOFORM 1S | Q9HCP0 | Casein kinase I gamma 1 isoform |
| ATF3_HUMAN ISOFORM 2 | P18847 | Cyclic-AMP-dependent transcription factor ATF-3 | KLK2_HUMAN ISOFORM 3 | P20151 | Glandular kallikrein 2 precursor |
| ATR_HUMAN MAJOR ISOFORM | Q9H6X2 | Anthrax toxin receptor precursor | KLKF_HUMAN ISOFORM 2 | Q9H2R5 | Kallikrein 15 precursor |
| B3G7_HUMAN ISOFORM 2 | Q9NY97 | Beta-1 3-galactosyltransferase 7 | LEF1_HUMAN ISOFORM B | Q9UJU2 | Lymphoid enhancer binding factor 1 |
| BC12_HUMAN ISOFORM 2 | Q9HB09 | Bcl-2 related proline-rich protein | LFA3_HUMAN ISOFORM SHORT | P19256 | Lymphocyte function-associated antigen 3 precursor |
| BMP1_HUMAN ISOFORM BMP1-4 | P13497 | Bone morphogenetic protein 1 precursor | LIK1_HUMAN ISOFORM 3 | P53667 | LIM domain kinase 1 |
| BMP1_HUMAN ISOFORM BMP1-5 | P13497 | Bone morphogenetic protein 1 precursor | LSHR_HUMAN MAJOR ISOFORM | P22888 | Lutropin-choriogonadotropic hormone receptor precursor |
| BMP1_HUMAN ISOFORM BMP1-6 | P13497 | Bone morphogenetic protein 1 precursor | LYST_HUMAN MAJOR ISOFORM | Q99698 | Lysosomal trafficking regulator |
| C343_HUMAN ISOFORM 4 | Q9HB55 | Cytochrome P450 3A43 | M2A2_HUMAN ISOFORM SHORT | P49641 | Alpha-mannosidase IIx |
| CA34_HUMAN MAJOR ISOFORM | Q01955 | Collagen alpha 3 | MADI_HUMAN ISOFORM 2 | O95405 | Mothers against decapentaplegic homolog interacting protein |

TABLE 1-continued

SWISS-PROT Protein isoforms characterized as targets of NMD.

| ISOFORM NAME | ACCESSION | PROTEIN DESCRIPTION | ISOFORM NAME | ACCESSION | PROTEIN DESCRIPTION |
|---|---|---|---|---|---|
| CA34_HUMAN ISOFORM 3 | Q01955 | Collagen alpha 3 | MAP2_HUMAN MAJOR ISOFORM | P11137 | Microtubule-associated protein 2 |
| CAL0_HUMAN ISOFORM 2 | P01258 | Calcitonin precursor [Contains: Calcitonin; Katacalcin] | MAP2_HUMAN ISOFORM MAP2C | P11137 | Microtubule-associated protein 2 |
| CANA_HUMAN ISOFORM B | Q9HC93 | Calpain 10 | MAP4_HUMAN ISOFORM 2 | P27816 | Microtubule-associated protein 4 |
| CANA_HUMAN ISOFORM D | Q9HC93 | Calpain 10 | MAX_HUMAN ISOFORM 3 | P25912 | Max protein |
| CANA_HUMAN ISOFORM E | Q9HC93 | Calpain 10 | MK11_HUMAN ISOFORM BETA-2 | Q15759 | Mitogen-activated protein kinase 11 |
| CANA_HUMAN ISOFORM F | Q9HC93 | Calpain 10 | MLH3_HUMAN ISOFORM 2 | Q9UHC1 | DNA mismatch repair protein Mlh3 |
| CBS_HUMAN MAJOR ISOFORM | P35520 | Cystathionine beta-synthase | MRP3_HUMAN ISOFORM 3A | O15438 | Canalicular multispecific organic anion transporter 2 |
| CD38_HUMAN ISOFORM 2 | P28907 | ADP-ribosyl cyclase 1 | MRP3_HUMAN ISOFORM 3B | O15438 | Canalicular multispecific organic anion transporter 2 |
| CD47_HUMAN ISOFORM OA3-305 | Q08722 | Leukocyte surface antigen CD47 precursor | MSRE_HUMAN ISOFORM 11 | P21757 | Macrophage scavenger receptor types I and II |
| CFLA_HUMAN ISOFORM 9 | O43618 | CASP8 and FADD-like apoptosis regulator precursor | MTF2_HUMAN MAJOR ISOFORM | Q9Y483 | Metal-response element-binding transcription factor 2 |
| CHRD_HUMAN ISOFORM 3 | Q9P0Z5 | Chordin precursor | NK31_HUMAN MAJOR ISOFORM | Q99801 | Homeobox protein Nkx-31 |
| CHRD_HUMAN ISOFORM 4 | Q9P0Z5 | Chordin precursor | NXF5_HUMAN MAJOR ISOFORM | Q9H1B4 | Nuclear RNA export factor 5 |
| CIQ2_HUMAN ISOFORM 3 | O43526 | Potassium voltage-gated channel subfamily KQT member 2 | NXF5_HUMAN ISOFORM B | Q9H1B4 | Nuclear RNA export factor 5 |
| CIW4_HUMAN ISOFORM 2 | Q9NYG8 | Potassium channel subfamily K member 4 | NXF5_HUMAN ISOFORM C | Q9H1B4 | Nuclear RNA export factor 5 |
| CLK1_HUMAN ISOFORM SHORT | P49759 | Protein kinase CLK1 | NXF5_HUMAN ISOFORM D | Q9H1B4 | Nuclear RNA export factor 5 |
| CLK2_HUMAN ISOFORM SHORT | P49760 | Protein kinase CLK2 | NXF5_HUMAN ISOFORM E | Q9H1B4 | Nuclear RNA export factor 5 |
| CLK3_HUMAN ISOFORM 2 | P49761 | Protein kinase CLK3 | PHMX_HUMAN ISOFORM 4 | Q96QS1 | Phemx protein |
| CML1_HUMAN MAJOR ISOFORM | Q99788 | Chemokine receptor-like 1 | PHMX_HUMAN ISOFORM 5 | Q96QS1 | Phemx protein |
| COG4_HUMAN ISOFORM 2 | Q9H9E3 | Conserved oligomeric Golgi complex component 4 | PML_HUMAN ISOFORM PML-3B | P29590 | Probable transcription factor PML |
| COLQ_HUMAN ISOFORM VII | Q9UP88 | Acetylcholinesterase collagenic tail peptide precursor | PPE1_HUMAN ISOFORM 2 | O14829 | Serine/threonine protein phosphatase with EF-hands-1 |
| CPXM_HUMAN ISOFORM 2 | Q96SM3 | Potential carboxypeptidase X precursor | PPT2_HUMAN ISOFORM 2 | Q9UMR5 | Palmitoyl-protein thioesterase 2 precursor |
| CRN1_HUMAN ISOFORM 4 | Q9NYD8 | Crooked neck-like protein 1 | PRD7_HUMAN MAJOR ISOFORM | Q9NQW5 | PR-domain zinc finger protein 7 |
| CRN1_HUMAN ISOFORM 5 | Q9NYD8 | Crooked neck-like protein 1 | PSA7_HUMAN ISOFORM 4 | O14818 | Proteasome subunit alpha type 7 |
| CT24_HUMAN ISOFORM 4 | Q9BUV8 | Protein C20orf24 | PSD4_HUMAN ISOFORM RPN10E | P55036 | 26S proteasome non-ATPase regulatory subunit 4 |
| CTGF_HUMAN MAJOR ISOFORM | P29279 | Connective tissue growth factor precursor | PSN1_HUMAN ISOFORM I-374 | P49768 | Presenilin 1 |
| CU07_HUMAN ISOFORM B | P57077 | Protein C21orf7 | PTPD_HUMAN MAJOR ISOFORM | P23468 | Protein-tyrosine phosphatase delta precursor |
| CU07_HUMAN ISOFORM C | P57077 | Protein C21orf7 | R51D_HUMAN ISOFORM 2 | O94908 | DNA repair protein RAD51 homolog 4 |
| CU18_HUMAN ISOFORM B | Q9NVD3 | Protein C21orf18 | RBMS_HUMAN MAJOR ISOFORM | Q93062 | RNA-binding protein with multiple splicing |
| CU63_HUMAN ISOFORM B | P58658 | Protein C21orf63 precursor | RED1_HUMAN MAJOR ISOFORM | P78563 | Double-stranded RNA-specific editase 1 |
| CU80_HUMAN ISOFORM B | Q9Y2G5 | Protein C21orf80 | RHD_HUMAN MAJOR ISOFORM | Q9UQ21 | Blood group Rh |
| CYB5_HUMAN | P00167 | Cytochrome b5 | RHD_HUMAN | Q9UQ21 | Blood group Rh |

TABLE 1-continued

SWISS-PROT Protein isoforms characterized as targets of NMD.

| ISOFORM NAME | ACCESSION | PROTEIN DESCRIPTION | ISOFORM NAME | ACCESSION | PROTEIN DESCRIPTION |
|---|---|---|---|---|---|
| DACA__HUMAN ISOFORM 2 | Q9BYJ9 | Dermatomyositis associated with cancer putative autoantigen-1 | ISOFORM 3 RYK__HUMAN MAJOR ISOFORM | P34925 | Tyrosine-protein kinase RYK precursor |
| DFFB__HUMAN ISOFORM BETA | O76075 | DNA fragmentation factor 40 kDa subunit | RYK__HUMAN ISOFORM 2 | P34925 | Tyrosine-protein kinase RYK precursor |
| DFFB__HUMAN ISOFORM DELTA | O76075 | DNA fragmentation factor 40 kDa subunit | SCA1__HUMAN ISOFORM 2 | O15126 | Secretory carrier-associated membrane protein 1 |
| DFFB__HUMAN ISOFORM GAMMA | O76075 | DNA fragmentation factor 40 kDa subunit | SEN7__HUMAN MAJOR ISOFORM | Q9BQF6 | Sentrin-specific protease 7 |
| DJB2__HUMAN MAJOR ISOFORM | P25686 | DnaJ homolog subfamily B member 2 | SFR5__HUMAN ISOFORM SRP40-2 | Q13243 | Splicing factor arginine/serine-rich 5 |
| DJB2__HUMAN ISOFORM 3 | P25686 | DnaJ homolog subfamily B member 2 | SHX2__HUMAN MAJOR ISOFORM | O60902 | Short stature homeobox protein 2 |
| DONS__HUMAN ISOFORM 2 | Q9NYP3 | Downstream of son gene protein | SNB2__HUMAN ISOFORM 2 | Q13425 | Beta-2-syntrophin |
| DONS__HUMAN ISOFORM 3 | Q9NYP3 | Downstream of son gene protein | SNXD__HUMAN ISOFORM 2 | Q9Y5W8 | Sorting nexin 13 |
| DPP3__HUMAN ISOFORM 2 | Q9NY33 | Dipeptidyl-peptidase III | SON__HUMAN ISOFORM C | Q9UPY0 | SON protein |
| DSCA__HUMAN ISOFORM SHORT | O60469 | Down syndrome cell adhesion molecule precursor | SON__HUMAN ISOFORM E | Q9UPY0 | SON protein |
| DTNB__HUMAN ISOFORM 3 | O60941 | Dystrobrevin beta | SUR5__HUMAN ISOFORM SURF5A | Q15528 | Surfeit locus protein 5 |
| EPA3__HUMAN MAJOR ISOFORM | P29320 | Ephrin type-A receptor 3 precursor | T10B__HUMAN MAJOR ISOFORM | O14763 | Tumor necrosis factor receptor superfamily member 10B precursor |
| ERAL__HUMAN ISOFORM HERA-B | O75616 | GTP-binding protein era homolog | T10B__HUMAN ISOFORM SHORT | O14763 | Tumor necrosis factor receptor superfamily member 10B precursor |
| ESR2__HUMAN ISOFORM 3 | Q9UHD3 | Estrogen receptor beta | TM31__HUMAN ISOFORM BETA | Q9BZY9 | Tripartite motif protein 31 |
| F263__HUMAN MAJOR ISOFORM | Q16875 | 6-phosphofructo-2-kinase/fructose-2 6-biphosphatase 3 | TNR6__HUMAN ISOFORM 2 | P25445 | Tumor necrosis factor receptor superfamily member 6 precursor |
| FAFY__HUMAN ISOFORM SHORT | O00507 | Probable ubiquitin carboxyl-terminal hydrolase FAF-Y | TNR6__HUMAN ISOFORM 3 | P25445 | Tumor necrosis factor receptor superfamily member 6 precursor |
| FCAR__HUMAN ISOFORM B-DELTA-S2 | P24071 | Immunoglobulin alpha Fc receptor precursor | TNR6__HUMAN ISOFORM 4 | P25445 | Tumor necrosis factor receptor superfamily member 6 precursor |
| FCE2__HUMAN MAJOR ISOFORM | P06734 | Low affinity immunoglobulin epsilon FC receptor | TNR6__HUMAN ISOFORM 5 | P25445 | Tumor necrosis factor receptor superfamily member 6 precursor |
| FTCD__HUMAN ISOFORM E | O95954 | Formimidoyltransferase-cyclodeaminase | TPA__HUMAN ISOFORM SHORT | P00750 | Tissue-type plasminogen activator precursor |
| FUT8__HUMAN ISOFORM 2 | Q9BYC5 | Alpha-(1,6)-fucosyltransferase | TPO__HUMAN MAJOR ISOFORM | P40225 | Thrombopoietin precursor |
| FXM1__HUMAN ISOFORM 2 | Q08050 | Forkhead box protein M1 | TR12__HUMAN ISOFORM 12 | Q99831 | Tumor necrosis factor receptor superfamily member 12 precursor |
| G72__HUMAN MAJOR ISOFORM | P59103 | Protein G72 | TR12__HUMAN ISOFORM 3 | Q99831 | Tumor necrosis factor receptor superfamily member 12 precursor |
| G72__HUMAN ISOFORM 2 | P59103 | Protein G72 | TR12__HUMAN ISOFORM 4 | Q99831 | Tumor necrosis factor receptor superfamily member 12 precursor |
| G8__HUMAN MAJOR ISOFORM | Q9UBA6 | G8 protein | TR12__HUMAN ISOFORM 5 | Q99831 | Tumor necrosis factor receptor superfamily member 12 precursor |
| GBR1__HUMAN ISOFORM 1E | Q9UBS5 | Gamma-aminobutyric acid type B receptor subunit 1 precursor | TR12__HUMAN ISOFORM 6 | Q99831 | Tumor necrosis factor receptor superfamily member 12 precursor |
| GCFC__HUMAN ISOFORM D | Q9Y5B6 | GC-rich sequence DNA-binding factor homolog | TR12__HUMAN ISOFORM 7 | Q99831 | Tumor necrosis factor receptor superfamily member 12 precursor |
| GCP2__HUMAN ISOFORM 2 | Q9BSJ2 | Gamma-tubulin complex component 2 | U713__HUMAN ISOFORM 2 | Q9BYM8 | Ubiquitin conjugating enzyme 7 interacting protein 3 |

TABLE 1-continued

SWISS-PROT Protein isoforms characterized as targets of NMD.

| ISOFORM NAME | ACCESSION | PROTEIN DESCRIPTION | ISOFORM NAME | ACCESSION | PROTEIN DESCRIPTION |
|---|---|---|---|---|---|
| GDNR_HUMAN ISOFORM 2 | P56159 | GDNF receptor alpha precursor | U713_HUMAN ISOFORM 4 | Q9BYM8 | Ubiquitin conjugating enzyme 7 interacting protein 3 |
| GLI2_HUMAN MAJOR ISOFORM | P10070 | Zinc finger protein GLI2 | USH3_HUMAN ISOFORM B | P58418 | Usher syndrome type 3 protein |
| GLI2_HUMAN ISOFORM BETA | P10070 | Zinc finger protein GLI2 | WS14_HUMAN ISOFORM 5 | Q9NP71 | Williams-Beuren syndrome chromosome region 14 protein |
| GLI2_HUMAN ISOFORM DELTA | P10070 | Zinc finger protein GLI2 | XE7_HUMAN ISOFORM SHORT | Q02040 | B-lymphocyte antigen precursor |
| GLI2_HUMAN ISOFORM GAMMA | P10070 | Zinc finger protein GLI2 | Z236_HUMAN ISOFORM A | Q9UL36 | Zinc finger protein 236 |
| GLSK_HUMAN ISOFORM GAC | O94925 | Glutaminase kidney isoform mitochondrial precursor | ZAN_HUMAN ISOFORM 1 | Q9BXN9 | Zonadhesin precursor |
| GPT_HUMAN MAJOR ISOFORM | Q9H3H5 | UDP-N-acetylglucosamine--dolichyl-phosphate N- | ZAN_HUMAN ISOFORM 2 | Q9BXN9 | Zonadhesin precursor |
| GRB2_HUMAN MAJOR ISOFORM | P29354 | Growth factor receptor-bound protein 2 | ZAN_HUMAN ISOFORM 4 | Q9BXN9 | Zonadhesin precursor |
| HAIR_HUMAN MAJOR ISOFORM | O43593 | Hairless protein | ZAN_HUMAN ISOFORM 5 | Q9BXN9 | Zonadhesin precursor |
| HAIR_HUMAN ISOFORM SHORT | O43593 | Hairless protein | | | |

What is claimed is:

1. A method for systematically characterizing putative protein isoforms as apparent targets of nonsense-mediated decay (NMD), the method comprising the following steps, each of which is performed with a suitably programmed computer:

identifying a dataset of target putative protein isoform sequences from a curated protein sequence database for characterization;

identifying from an mRNA dataset corresponding mRNA sequences representing transcripts encoding the protein isoforms, wherein each of the transcripts comprises a termination codon and a final intron;

determining corresponding gene intron-exon structures by mapping the mRNA sequences to corresponding genomic sequences;

determining if the transcripts are apparent targets of NMD by comparing the position of the termination codon to the position of the final intron, wherein if the termination codon of the transcript is more than 50 nucleotides upstream of the final intron position, then the transcript is an apparent target of NMD; and outputting from the computer a list of said isoforms that are apparent targets of NMD, wherein the dataset of target putative protein isoform sequences comprises a subset of the isoforms of Table 1:

TABLE 1

Protein isoforms characterized as targets of NMD.

| ISOFORM NAME | ACCESSION | PROTEIN DESCRIPTION |
|---|---|---|
| 3BP2_HUMANISOFORM SHORT | P78314 | SH3 domain-binding protein 2 |
| 5H4_HUMANMAJOR ISOFORM | Q13639 | 5-hydroxytryptamine 4 receptor |
| A1A1_HUMANISOFORM SHORT | P05023 | Sodium/potassium-transporting ATPase alpha-1 chain precursor |
| ABCD_HUMANISOFORM 2 | Q9NSE7 | Putative ATP-binding cassette transporter C13 |
| ABCD_HUMANISOFORM FORM 3 | Q9NSE7 | Putative ATP-binding cassette transporter C13 |
| AD11_HUMANISOFORM SHORT | O75078 | ADAM 11 precursor |
| AD12_HUMANMAJOR ISOFORM | O43184 | ADAM 12 precursor |
| AD22_HUMANISOFORM 2 | Q9POK1 | ADAM 22 precursor |
| AKP1_HUMANISOFORM 2 | Q92667 | A kinase anchor protein 1 mitochondrial precursor |
| ANPB_HUMANISOFORM SHORT | P20594 | Atrial natriuretic peptide receptor B precursor |
| AS13_HUMANMAJOR ISOFORM | Q8WXK3 | Ankyrin repeat and SOCS box containing protein 13 |
| AS13_HUMANISOFORM 2 | Q8WXK3 | Ankyrin repeat and SOCS box containing protein 13 |
| ATF3_HUMANISOFORM 2 | P18847 | Cyclic-AMP-dependent transcription factor ATF-3 |
| ATR_HUMANMAJOR ISOFORM | Q9H6X2 | Anthrax toxin receptor precursor |
| B3G7_HUMANISOFORM 2 | Q9NY97 | Beta-1 3-galactosyltransferase 7 |
| BC12_HUMANISOFORM 2 | Q9HB09 | Bcl-2 related proline-rich protein |
| BMP1_HUMANISOFORM BMP1-4 | P13497 | Bone morphogenetic protein 1 precursor |
| BMP1_HUMANISOFORM BMP1-5 | P13497 | Bone morphogenetic protein 1 precursor |
| BMP1_HUMANISOFORM BMP1-6 | P13497 | Bone morphogenetic protein 1 precursor |
| C343_HUMANISOFORM 4 | Q9HB55 | Cytochrome P450 3A43 |
| CA34_HUMANMAJOR ISOFORM | Q01955 | Collagen alpha 3 |
| CA34_HUMANISOFORM 3 | Q01955 | Collagen alpha 3 |
| CAL0_HUMANISOFORM 2 | P01258 | Calcitonin precursor [Contains: Calcitonin; Katacalcin |
| CANA_HUMANISOFORM B | Q9HC93 | Calpain 10 |
| CANA_HUMANISOFORM D | Q9HC93 | Calpain 10 |
| CANA_HUMANISOFORM | Q9HC93 | Calpain 10 |

TABLE 1-continued

Protein isoforms characterized as targets of NMD.

| ISOFORM NAME | ACCESSION | PROTEIN DESCRIPTION |
|---|---|---|
| FORM E | | |
| CANA_HUMANISO FORM F | Q9HC93 | Calpain 10 |
| CBS_HUMANMAJOR ISOFORM | P35520 | Cystathionine beta-synthase |
| CD38_HUMANISO FORM 2 | P28907 | ADP-ribosyl cyclase 1 |
| CD47_HUMANISO FORM OA3-305 | Q08722 | Leukocyte surface antigen CD47 precursor |
| CFLA_HUMANISO FORM 9 | O43618 | CASP8 and FADD-like apoptosis regulator precursor |
| CHRD_HUMANISO FORM 3 | Q9P0Z5 | Chordin precursor |
| CHRD_HUMANISO FORM 4 | Q9P0Z5 | Chordin precursor |
| CIQ2_HUMANISO FORM 3 | O43526 | Potassium voltage-gated channel subfamily KQT member 2 |
| CIW4_HUMANISO FORM 2 | Q9NYG8 | Potassium channel subfamily K member 4 |
| CLK1_HUMANISO FORM SHORT | P49759 | Protein kinase CLK1 |
| CLK2_HUMANISO FORM SHORT | P49760 | Protein kinase CLK2 |
| CLK3_HUMANISO FORM 2 | P49761 | Protein kinase CLK3 |
| CML1_HUMANMAJOR ISOFORM | Q99788 | Chemokine receptor-like 1 |
| COG4_HUMANISO FORM 2 | Q9H9E3 | Conserved oilgomeric Golgi complex component 4 |
| COLQ_HUMANISO FORM VII | Q9UP88 | Acetylcholinesterase collagenic tail peptide precursor |
| CPXM_HUMANISO FORM 2 | Q96SM3 | Potential carboxypeptidase X precursor |
| CRN1_HUMANISO FORM 4 | Q9NYD8 | Crooked neck-like protein 1 |
| CRN1_HUMANISO FORM 5 | Q9NYD8 | Crooked neck-like protein 1 |
| CT24_HUMANISO FORM 4 | Q9BUV8 | Protein C20orf24 |
| CTGF_HUMANMAJOR ISOFORM | P29279 | Connective tissue growth factor precursor |
| CU07_HUMANISO FORM B | P57077 | Protein C21orf7 |
| CU07_HUMANISO FORM C | P57077 | Protein C21orf7 |
| CU18_HUMANISO FORM B | Q9NVD3 | Protein C21orf18 |
| CU63_HUMANISO FORM B | P58658 | Protein C21orf63 precursor |
| CU80_HUMANISO FORM B | Q9Y2G5 | Protein C21orf80 |
| CYB5_HUMANISO FORM 2 | P00167 | Cytochrome b5 |
| DACA_HUMANISO FORM 2 | Q9BYJ9 | Dermatomyositis associated with cancer putative autoantigen-1 |
| DFFB_HUMANISO FORM BETA | O76075 | DNA fragmentation factor 40 kDa subunit |
| DFFB_HUMANISO FORM DELTA | O76075 | DNA fragmentation factor 40 kDa subunit |
| DFFB_HUMANISO FORM GAMMA | O76075 | DNA fragmentation factor 40 kDa subunit |
| DJB2_HUMANMAJOR ISOFORM | P25686 | DnaJ homolog subfamily B member 2 |
| DJB2_HUMANISO FORM 3 | P25686 | DnaJ homolog subfamily B member 2 |
| DONS_HUMANISO FORM 2 | Q9NYP3 | Downstream of son gene protein |
| DONS_HUMANISOFORM 3 | Q9NYP3 | Downstream of son gene protein |
| DPP3_HUMANISO FORM 2 | Q9NY33 | Dipeptidyl-peptidase III |
| DSCA_HUMANISO FORM SHORT | O60469 | Down syndrome cell adhesion molecule precursor |
| DTNB_HUMANISO FORM 3 | O60941 | Dystrobrevin beta |
| EPA3_HUMANMAJOR ISOFORM | P29320 | Ephrin type-A receptor 3 precursor |
| ERAL_HUMANISO FORM HERA-B | O75616 | GTP-binding protein era homolog |
| ESR2_HUMANISO FORM 3 | Q9UHD3 | Estrogen receptor beta |
| F263_HUMANMAJOR ISOFORM | Q16875 | 6-phosphofructo-2-kinase/fructose-2 6-biphosphatase 3 |
| FAFY_HUMANISO FORM SHORT | O00507 | Probable ubiquitin carboxyl-terminal hydrolase FAF-Y |
| FCAR_HUMANISO FORM B-DELTA-S2 | P24071 | Immunoglobulin alpha Fc receptor precursor |
| FCE2_HUMANMAJOR ISOFORM | P06734 | Low affinity immunoglobulin epsilon FC receptor |
| FTCD_HUMANISO FORM E | O95954 | Formimidoyltransferase-cyclodeaminase |
| FUT8_HUMANISO FORM 2 | Q9BYC5 | Alpha-(1,6)-fucosyltransferase |
| FXM1_HUMANISO FORM 2 | Q08050 | Forkhead box protein M1 |
| G72_HUMANMAJOR ISOFORM | P59103 | Protein G72 |
| G72_HUMANISO FORM 2 | P59103 | Protein G72 |
| G8_HUMANMAJOR ISOFORM | Q9UBA6 | G8 protein |
| GBR1_HUMANISO FORM 1E | Q9UBS5 | Gamma-aminobutyric acid type B receptor subunit 1 precursor |
| GCFC_HUMANISO FORM D | Q9Y5B6 | GC-rich sequence DNA-binding factor homolog |
| GCP2_HUMANISO FORM 2 | Q9BSJ2 | Gamma-tubulin complex component 2 |
| GDNR_HUMANISO FORM 2 | P56159 | GDNF receptor alpha precursor |
| GLI2_HUMANMAJOR ISOFORM | P10070 | Zinc finger protein GLI2 |
| GLI2_HUMANISO FORM BETA | P10070 | Zinc finger protein GLI2 |
| GLI2_HUMANISO FORM DELTA | P10070 | Zinc finger protein GLI2 |
| GLI2_HUMANISO FORM GAMMA | P10070 | Zinc finger protein GLI2 |
| GLSK_HUMANISO FORM GAC | O94925 | Glutaminase kidney isoform mitochondrial precursor |
| GPT_HUMANMAJOR ISOFORM | Q9H3H5 | UDP-N-acetylglucosamine--dolichyl-phosphate N- |
| GRB2_HUMANMAJOR ISOFORM | P29354 | Growth factor receptor-bound protein 2 |
| HAIR_HUMANMAJOR ISOFORM | O43593 | Hairless protein |
| HAIR_HUMANISO FORM SHORT | O43593 | Hairless protein |
| HFE_HUMANMAJOR ISOFORM | Q9HC68 | Hereditary hemochromatosis protein precursor |
| I17S_HUMANISO FORM 2 | Q9NRM6 | Interleukin-17B receptor precursor |
| ICE2_HUMANISO FORM ICH-1S | P42575 | Caspase-2 precursor |
| ICE8_HUMANISO FORM 7 | Q9C0K4 | Caspase-8 precursor |
| ICEA_HUMANISO FORM B | Q92851 | Caspase-10 precursor |
| ICEA_HUMANISO FORM C | Q92851 | Caspase-10 precursor |
| ILF1_HUMANISO FORM 2 | Q01167 | Interleukin enhancer-binding factor 1 |
| IRF7_HUMANISO FORM C | Q92985 | Interferon regulatory factor 7 |
| IRL1_HUMANISO FORM C | Q01638 | Interleukin 1 receptor-like 1 precursor |

TABLE 1-continued

Protein isoforms characterized as targets of NMD.

| ISOFORM NAME | ACCESSION | PROTEIN DESCRIPTION |
|---|---|---|
| ITP1_HUMANMAJOR ISOFORM | O14713 | Integrin beta-1 binding protein 1 |
| ITP1_HUMANISO FORM 2 | O14713 | Integrin beta-1 binding protein 1 |
| KC11_HUMANIS OFORM 1S | Q9HCP0 | Casein kinase I gamma 1 isoform |
| KLK2_HUMANIS OFORM 3 | P20151 | Glandular kallikrein 2 precursor |
| KLKF_HUMANISO FORM 2 | Q9H2R5 | Kallikrein 15 precursor |
| LEF1_HUMANISO FORM B | Q9UJU2 | Lymphoid enhancer binding factor 1 |
| LFA3_HUMANISO FORM SHORT | P19256 | Lymphocyte function-associated antigen 3 precursor |
| LIK1_HUMANISO FORM 3 | P53667 | LIM domain kinase 1 |
| LSHR_HUMANMAJOR ISOFORM | P22888 | Lutropin-choriogonadotropic hormone receptor precursor |
| LYST_HUMANMAJOR ISOFORM | Q99698 | Lysosomal trafficking regulator |
| M2A2_HUMANISO FORM SHORT | P49641 | Alpha-mannosidase IIx |
| MAD1_HUMANISO FORM 2 | O95405 | Mothers against decapentaplegic homolog interacting protein |
| MAP2_HUMAN MAJOR ISOFORM | P11137 | Microtubule-associated protein 2 |
| MAP2_HUMANI SOFORM MAP2C | P11137 | Microtubule-associated protein 2 |
| MAP4_HUMANI SOFORM 2 | P27816 | Microtubule-associated protein 4 |
| MAX_HUMANISO FORM 3 | P25912 | Max protein |
| MK11_HUMANISO FORM BETA-2 | Q15759 | Mitogen-activated protein kinase 11 |
| MLH3_HUMANISO FORM 2 | Q9UHC1 | DNA mismatch repair protein Mlh3 |
| MRP3_HUMANISO FORM 3A | O15438 | Canalicular multispecific organic anion transporter 2 |
| MRP3_HUMANISO FORM 3B | O15438 | Canalicular multispecific organic anion transporter 2 |
| MSRE_HUMANISO FORM II | P21757 | Macrophage scavenger receptor types I and II |
| MTF2_HUMANMAJOR ISOFORM | Q9Y483 | Metal-response element-binding transcription factor 2 |
| NK31_HUMANMAJOR ISOFORM | Q99801 | Homeobox protein Nkx-31 |
| NXF5_HUMANMAJOR ISOFORM | Q9H1B4 | Nuclear RNA export factor 5 |
| NXFS_HUMANISO FORM B | Q9H1B4 | Nuclear RNA export factor 5 |
| NXFS_HUMANISO FORM C | Q9H1B4 | Nuclear RNA export factor 5 |
| NXF5_HUMANISO FORM D | Q9H1B4 | Nuclear RNA export factor 5 |
| NXFS_HUMANISO FORM E | Q9H1B4 | Nuclear RNA export factor 5 |
| PHMX_HUMANISO FORM 4 | Q96QS1 | Phemx protein |
| PHMX_HUMANISO FORM 5 | Q96QS1 | Phemx protein |
| PML_HUMANISO FORM PML-3B | P29590 | Probable transcription factor PML |
| PPE1_HUMANISO FORM 2 | O14829 | Serine/threonine protein phosphatase with EF-hands-1 |
| PPT2_HUMANISO FORM 2 | Q9UMR5 | Palmitoyl-protein thioesterase 2 precursor |
| PRD7_HUMANMAJOR ISOFORM | Q9NQW5 | PR-domain zinc finger protein 7 |
| PSA7_HUMANISO FORM 4 | O14818 | Proteasome subunit alpha type 7 |
| PSD4_HUMANISO FORM RPN10E | P55036 | 26S proteasome non-ATPase regulatory subunit 4 |
| PSN1_HUMANISO FORM I-374 | P49768 | Presenilin 1 |
| PTPD_HUMANMAJOR ISOFORM | P23468 | Protein-tyrosine phosphatase delta precursor |
| R51D_HUMANISO FORM 2 | O94908 | DNA repair protein RAD51 homolog 4 |
| RBMS_HUMAN MAJOR ISOFORM | Q93062 | RNA-binding protein with multiple splicing |
| RED1_HUMANMAJOR ISOFORM | P78563 | Double-stranded RNA-specific editase 1 |
| RHD_HUMANMAJOR ISOFORM | Q9UQ21 | Blood group Rh |
| RHD_HUMANISO FORM 3 | Q9UQ21 | Blood group Rh |
| RYK_HUMANMAJOR ISOFORM | P34925 | Tyrosine-protein kinase RYK precursor |
| RYK_HUMANIS OFORM 2 | P34925 | Tyrosine-protein kinase RYK precursor |
| SCA1_HUMANISO FORM 2 | O15126 | Secretory carrier-associated membrane protein 1 |
| SEN7_HUMANMAJOR ISOFORM | Q9BQF6 | Sentrin-specific protease 7 |
| SFR5_HUMANISO FORM SRP40-2 | Q13243 | Splicing factor arginine/serine-rich 5 |
| SHX2_HUMANMAJOR ISOFORM | O60902 | Short stature homeobox protein 2 |
| SNB2_HUMANISO FORM 2 | Q13425 | Beta-2-syntrophin |
| SNXD_HUMANISO FORM 2 | Q9Y5W8 | Sorting nexin 13 |
| SON_HUMANISO FORM C | Q9UPY0 | SON protein |
| SON_HUMANISO FORM E | Q9UPY0 | SON protein |
| SUR5_HUMANISO FORM SURF5A | Q15528 | Surfeit locus protein 5 |
| T10B_HUMANMAJOR ISOFORM | O14763 | Tumor necrosis factor receptor superfamily member 10B precursor |
| T10B_HUMANISO FORM SHORT | O14763 | Tumor necrosis factor receptor superfamily member 10B precursor |
| TM31_HUMANISO FORM BETA | Q9BZY9 | Tripartite motif protein 31 |
| TNR6_HUMANISO FORM 2 | P25445 | Tumor necrosis factor receptor superfamily member 6 precursor |
| TNR6_HUMANISO FORM 3 | P25445 | Tumor necrosis factor receptor superfamily member 6 precursor |
| TNR6_HUMANISO FORM 4 | P25445 | Tumor necrosis factor receptor superfamily member 6 precursor |
| TNR6_HUMANISO FORM 5 | P25445 | Tumor necrosis factor receptor superfamily member 6 precursor |
| TPA_HUMANISO FORM SHORT | P00750 | Tissue-type plasminogen activator precursor |
| TPO_HUMANMAJOR ISOFORM | P40225 | Thrombopoietin precursor |
| TR12_HUMANISO FORM 12 | Q99831 | Tumor necrosis factor receptor superfamily member 12 precursor |
| TR12_HUMANISO FORM 3 | Q99831 | Tumor necrosis factor receptor superfamily member 12 precursor |
| TR12_HUMANISO FORM 4 | Q99831 | Tumor necrosis factor receptor superfamily member 12 precursor |
| TR12_HUMANISO FORM 5 | Q99831 | Tumor necrosis factor receptor superfamily member 12 precursor |
| TR12_HUMANISO | Q99831 | Tumor necrosis factor |

TABLE 1-continued

Protein isoforms characterized as targets of NMD.

| ISOFORM NAME | ACCESSION | PROTEIN DESCRIPTION |
|---|---|---|
| FORM 6 | | receptor superfamily member 12 precursor |
| TR12_HUMANISO FORM 7 | Q99831 | Tumor necrosis factor receptor superfamily member 12 precursor |
| U7I3_HUMANISO FORM 2 | Q9BYM8 | Ubiquitin conjugating enzyme 7 interacting protein 3 |
| U7I3_HUMANISO FORM 4 | Q9BYM8 | Ubiquitin conjugating enzyme 7 interacting protein 3 |
| USH3_HUMANISO FORM B | P58418 | Usher syndrome type 3 protein |
| WS14_HUMANISO FORM 5 | Q9NP71 | Williams-Beuren syndrome chromosome region 14 protein |
| XE7_HUMANISO FORM SHORT | Q02040 | B-lymphocyte antigen precursor |
| Z236_HUMANISO FORM A | Q9UL36 | Zinc finger protein 236 |
| ZAN_HUMANISO FORM 1 | Q9BXN9 | Zonadhesin precursor |
| ZAN_HUMANISO FORM 2 | Q9BXN9 | Zonadhesin precursor |
| ZAN_HUMANISO FORM 4 | Q9BXN9 | Zonadhesin precursor |
| ZAN_HUMANISO FORM 5. | Q9BXN9 | Zonadhesin precursor |

2. The method of claim 1 wherein the dataset of target putative protein isoform sequences comprises isoforms of Calpain-10, CLK1, CLK2, CLK3, and LARD/TNFRSF12.

3. A method for systematically characterizing putative protein isoforms as apparent targets of nonsense-mediated decay (NMD), the method comprising the following steps, each of which is performed with a suitably programmed computer:

identifying a dataset of target putative protein isoform sequences from a curated protein sequence database for characterization;

identifying corresponding gene intron-exon structures by mapping corresponding mRNA sequences of an mRNA sequence dataset to genomic sequences of a genomic DNA sequence dataset;

screening the isoform dataset for a subset of isoforms encoded by transcripts comprising alternate splices which introduce a stop codon more than 50 nucleotides upstream of the final exon-exon splice junction; and classifying the subset isoforms as being encoded by transcripts comprising premature stop codons and as targets of NMD; and outputting from the computer a list of said isoforms that are apparent targets of NMD, wherein the dataset of target putative protein isoform sequences comprises a subset of the isoforms of Table 1:

TABLE 1

Protein isoforms characterized as targets of NMD.

| ISOFORM NAME | ACCESSION | PROTEIN DESCRIPTION |
|---|---|---|
| 3BP2_HUMANISO FORM SHORT | P78314 | SH3 domain-binding protein 2 |
| 5H4_HUMANMAJOR ISOFORM | Q13639 | 5-hydroxytryptamine 4 receptor |
| A1A1_HUMANISO FORM SHORT | P05023 | Sodium/potassium-transporting ATPase alpha-1 chain precursor |

TABLE 1-continued

Protein isoforms characterized as targets of NMD.

| ISOFORM NAME | ACCESSION | PROTEIN DESCRIPTION |
|---|---|---|
| ABCD_HUMANISO FORM 2 | Q9NSE7 | Putative ATP-binding cassette transporter C13 |
| ABCD_HUMANISO FORM 3 | Q9NSE7 | Putative ATP-binding cassette transporter C13 |
| AD11_HUMANISO FORM SHORT | O75078 | ADAM 11 precursor |
| AD12_HUMANMAJOR ISOFORM | O43184 | ADAM 12 precursor |
| AD22_HUMANISO FORM 2 | Q9POK1 | ADAM 22 precursor |
| AKP1_HUMANISO FORM 2 | Q92667 | A kinase anchor protein 1 mitochondrial precursor |
| ANPB_HUMANISO FORM SHORT | P20594 | Atrial natriuretic peptide receptor B precursor |
| AS13_HUMANMAJOR ISOFORM | Q8WXK3 | Ankyrin repeat and SOCS box containing protein 13 |
| AS13_HUMANISO FORM 2 | Q8WXK3 | Ankyrin repeat and SOCS box containing protein 13 |
| ATF3_HUMANISO FORM 2 | P18847 | Cyclic-AMP-dependent transcription factor ATF-3 |
| ATR_HUMANMAJOR ISOFORM | Q9H6X2 | Anthrax toxin receptor precursor |
| B3G7_HUMANISO FORM 2 | Q9NY97 | Beta-1 3-galactosyltransferase 7 |
| BC12_HUMANISO FORM 2 | Q9HB09 | Bcl-2 related proline-rich protein |
| BMP1_HUMANISO FORM BMP1-4 | P13497 | Bone morphogenetic protein 1 precursor |
| BMP1_HUMANISO FORM BMP1-5 | P13497 | Bone morphogenetic protein 1 precursor |
| BMP1_HUMANISO FORM BMP1-6 | P13497 | Bone morphogenetic protein 1 precursor |
| C343_HUMANISO FORM 4 | Q9HB55 | Cytochrome P450 3A43 |
| CA34_HUMANMAJOR ISOFORM | Q01955 | Collagen alpha 3 |
| CA34_HUMANISO FORM 3 | Q01955 | Collagen alpha 3 |
| CAL0_HUMANISO FORM 2 | P01258 | Calcitonin precursor [Contains: Calcitonin; Katacalcin |
| CANA_HUMANISO FORM B | Q9HC93 | Calpain 10 |
| CANA_HUMANISO FORM D | Q9HC93 | Calpain 10 |
| CANA_HUMANISO FORM E | Q9HC93 | Calpain 10 |
| CANA_HUMANISO FORM F | Q9HC93 | Calpain 10 |
| CBS_HUMANMAJOR ISOFORM | P35520 | Cystathionine beta-synthase |
| CD38_HUMANISO FORM 2 | P28907 | ADP-ribosyl cyclase 1 |
| CD47_HUMANISO FORM OA3-305 | Q08722 | Leukocyte surface antigen CD47 precursor |
| CFLA_HUMANISO FORM 9 | O43618 | CASP8 and FADD-like apoptosis regulator precursor |
| CHRD_HUMANISO FORM 3 | Q9P0Z5 | Chordin precursor |
| CHRD_HUMANISO FORM 4 | Q9P0Z5 | Chordin precursor |
| CIQ2_HUMANISO FORM 3 | O43526 | Potassium voltage-gated channel subfamily KQT member 2 |
| CIW4_HUMANISO FORM 2 | Q9NYG8 | Potassium channel subfamily K member 4 |
| CLK1_HUMANISO FORM SHORT | P49759 | Protein kinase CLK1 |
| CLK2_HUMANISO FORM SHORT | P49760 | Protein kinase CLK2 |
| CLK3_HUMANISO FORM 2 | P49761 | Protein kinase CLK3 |
| CML1_HUMANMAJOR ISOFORM | Q99788 | Chemokine receptor-like 1 |
| COG4_HUMANISO FORM 2 | Q9H9E3 | Conserved oligomeric Golgi complex component 4 |
| COLQ_HUMANISO | Q9UP88 | Acetylcholinesterase |

TABLE 1-continued

Protein isoforms characterized as targets of NMD.

| ISOFORM NAME | ACCESSION | PROTEIN DESCRIPTION |
|---|---|---|
| FORM VII | | collagenic tail peptide precursor |
| CPXM_HUMANISO FORM 2 | Q96SM3 | Potential carboxypeptidase X precursor |
| CRN1_HUMANISO FORM 4 | Q9NYD8 | Crooked neck-like protein 1 |
| CRN1_HUMANISO FORM 5 | Q9NYD8 | Crooked neck-like protein 1 |
| CT24_HUMANISO FORM 4 | Q9BUV8 | Protein C20orf24 |
| CTGF_HUMANMAJOR ISOFORM | P29279 | Connective tissue growth factor precursor |
| CU07_HUMANISO FORM B | P57077 | Protein C21orf7 |
| CU07_HUMANISO FORM C | P57077 | Protein C21orf7 |
| CU18_HUMANISO FORM B | Q9NVD3 | Protein C21orf18 |
| CU63_HUMANISO FORM B | P58658 | Protein C21orf63 precursor |
| CU80_HUMANISO FORM B | Q9Y2G5 | Protein C21orf80 |
| CYB5_HUMANISO FORM 2 | P00167 | Cytochrome b5 |
| DACA_HUMANISO FORM 2 | Q9BYJ9 | Dermatomyositis associated with cancer putative autoantigen-1 |
| DFFB_HUMANISO FORM BETA | O76075 | DNA fragmentation factor 40 kDa subunit |
| DFFB_HUMANISO FORM DELTA | O76075 | DNA fragmentation factor 40 kDa subunit |
| DFFB_HUMANISO FORM GAMMA | O76075 | DNA fragmentation factor 40 kDa subunit |
| DJB2_HUMANMAJOR ISOFORM | P25686 | DnaJ homolog subfamily B member 2 |
| DJB2_HUMANISO FORM 3 | P25686 | DnaJ homolog subfamily B member 2 |
| DONS_HUMANISO FORM 2 | Q9NYP3 | Downstream of son gene protein |
| DONS_HUMANIS OFORM 3 | Q9NYP3 | Downstream of son gene protein |
| DPP3_HUMANISO FORM 2 | Q9NY33 | Dipeptidyl-peptidase III |
| DSCA_HUMANISO FORM SHORT | O60469 | Down syndrome cell adhesion molecule precursor |
| DTNB_HUMANISO FORM 3 | O60941 | Dystrobrevin beta |
| EPA3_HUMANMAJOR ISOFORM | P29320 | Ephrin type-A receptor 3 precursor |
| ERAL_HUMANISO FORM HERA-B | O75616 | GTP-binding protein era homolog |
| ESR2_HUMANISO FORM 3 | Q9UHD3 | Estrogen receptor beta |
| F263_HUMANMAJOR ISOFORM | Q16875 | 6-phosphofructo-2-kinase/fructose-2 6-biphosphatase 3 |
| FAFY_HUMANISO FORM SHORT | O00507 | Probable ubiquitin carboxyl-terminal hydrolase FAF-Y |
| FCAR_HUMANISO FORM B-DELTA-S2 | P24071 | Immunoglobulin alpha Fc receptor precursor |
| FCE2_HUMANMAJOR ISOFORM | P06734 | Low affinity immunoglobulin epsilon FC receptor |
| FTCD_HUMANISO FORM E | O95954 | Formimidoyltransferase-cyclodeaminase |
| FUT8_HUMANISO FORM 2 | Q9BYC5 | Alpha-(1,6)-fucosyltransferase |
| FXM1_HUMANISO FORM 2 | Q08050 | Forkhead box protein M1 |
| G72_HUMANMAJOR ISOFORM | P59103 | Protein G72 |
| G72_HUMANISO FORM 2 | P59103 | Protein G72 |
| G8_HUMANMAJOR ISOFORM | Q9UBA6 | G8 protein |
| GBR1_HUMANISO | Q9UBS5 | Gamma-aminobutyric acid |

TABLE 1-continued

Protein isoforms characterized as targets of NMD.

| ISOFORM NAME | ACCESSION | PROTEIN DESCRIPTION |
|---|---|---|
| FORM 1E | | type B receptor subunit 1 precursor |
| GCFC_HUMANISO FORM D | Q9Y5B6 | GC-rich sequence DNA-binding factor homolog |
| GCP2_HUMANISO FORM 2 | Q9BSJ2 | Gamma-tubulin complex component 2 |
| GDNR_HUMANISO FORM 2 | P56159 | GDNF receptor alpha precursor |
| GLI2_HUMANMAJOR ISOFORM | P10070 | Zinc finger protein GLI2 |
| GLI2_HUMANISO FORM BETA | P10070 | Zinc finger protein GLI2 |
| GLI2_HUMANISO FORM DELTA | P10070 | Zinc finger protein GLI2 |
| GLI2_HUMANISO FORM GAMMA | P10070 | Zinc finger protein GLI2 |
| GLSK_HUMANISO FORM GAC | O94925 | Glutaminase kidney isoform mitochondrial precursor |
| GPT_HUMANMAJOR ISOFORM | Q9H3H5 | UDP-N-acetylglucosamine--dolichyl-phosphate N- |
| GRB2_HUMANMAJOR ISOFORM | P29354 | Growth factor receptor-bound protein 2 |
| HAIR_HUMANMAJOR ISOFORM | O43593 | Hairless protein |
| HAIR_HUMANISO FORM SHORT | O43593 | Hairless protein |
| HFE_HUMANMAJOR ISOFORM | Q9HC68 | Hereditary hemochromatosis protein precursor |
| I17S_HUMANISO FORM 2 | Q9NRM6 | Interleukin-17B receptor precursor |
| ICE2_HUMANISO FORM ICH-1S | P42575 | Caspase-2 precursor |
| ICE8_HUMANISO FORM 7 | Q9C0K4 | Caspase-8 precursor |
| ICEA_HUMANISO FORM B | Q92851 | Caspase-10 precursor |
| ICEA_HUMANISO FORM C | Q92851 | Caspase-10 precursor |
| ILF1_HUMANISO FORM 2 | Q01167 | Interleukin enhancer-binding factor 1 |
| IRF7_HUMANISO FORM C | Q92985 | Interferon regulatory factor 7 |
| IRL1_HUMANISO FORM C | Q01638 | Interleukin 1 receptor-like 1 precursor |
| ITP1_HUMANMAJOR ISOFORM | O14713 | Integrin beta-1 binding protein 1 |
| ITP1_HUMANISO FORM 2 | O14713 | Integrin beta-1 binding protein 1 |
| KC11_HUMANIS OFORM 1S | Q9HCP0 | Casein kinase I gamma 1 isoform |
| KLK2_HUMANIS OFORM 3 | P20151 | Glandular kallikrein 2 precursor |
| KLKF_HUMANISO FORM 2 | Q9H2R5 | Kallikrein 15 precursor |
| LEF1_HUMANISO FORM B | Q9UJU2 | Lymphoid enhancer binding factor 1 |
| LFA3_HUMANISO FORM SHORT | P19256 | Lymphocyte function-associated antigen 3 precursor |
| LIK1_HUMANISO FORM 3 | P53667 | LIM domain kinase 1 |
| LSHR_HUMANMAJOR ISOFORM | P22888 | Lutropin-choriogonadotropic hormone receptor precursor |
| LYST_HUMANMAJOR ISOFORM | Q99698 | Lysosomal trafficking regulator |
| M2A2_HUMANISO FORM SHORT | P49641 | Alpha-mannosidase IIx |
| MADI_HUMANISO FORM 2 | O95405 | Mothers against decapentaplegic homolog interacting protein |
| MAP2_HUMAN MAJOR ISOFORM | P11137 | Microtubule-associated protein 2 |
| MAP2_HUMANI | P11137 | Microtubule-associated |

TABLE 1-continued

Protein isoforms characterized as targets of NMD.

| ISOFORM NAME | ACCESSION | PROTEIN DESCRIPTION |
|---|---|---|
| SOFORM MAP2C | | protein 2 |
| MAP4_HUMANISOFORM 2 | P27816 | Microtubule-associated protein 4 |
| MAX_HUMANISOFORM 3 | P25912 | Max protein |
| MK11_HUMANISOFORM BETA-2 | Q15759 | Mitogen-activated protein kinase 11 |
| MLH3_HUMANISOFORM 2 | Q9UHC1 | DNA mismatch repair protein Mlh3 |
| MRP3_HUMANISOFORM 3A | O15438 | Canalicular multispecific organic anion transporter 2 |
| MRP3_HUMANISOFORM 3B | O15438 | Canalicular multispecific organic anion transporter 2 |
| MSRE_HUMANISOFORM II | P21757 | Macrophage scavenger receptor types I and II |
| MTF2_HUMANMAJOR ISOFORM | Q9Y483 | Metal-response element-binding transcription factor 2 |
| NK31_HUMANMAJOR ISOFORM | Q99801 | Homeobox protein Nkx-31 |
| NXF5_HUMANMAJOR ISOFORM | Q9H1B4 | Nuclear RNA export factor 5 |
| NXF5_HUMANISOFORM B | Q9H1B4 | Nuclear RNA export factor 5 |
| NXF5_HUMANISOFORM C | Q9H1B4 | Nuclear RNA export factor 5 |
| NXF5_HUMANISOFORM D | Q9H1B4 | Nuclear RNA export factor 5 |
| NXF5_HUMANISOFORM E | Q9H1B4 | Nuclear RNA export factor 5 |
| PHMX_HUMANISOFORM 4 | Q96QS1 | Phemx protein |
| PHMX_HUMANISOFORM 5 | Q96QS1 | Phemx protein |
| PML_HUMANISOFORM PML-3B | P29590 | Probable transcription factor PML |
| PPE1_HUMANISOFORM 2 | O14829 | Serine/threonine protein phosphatase with EF-hands-1 |
| PPT2_HUMANISOFORM 2 | Q9UMR5 | Palmitoyl-protein thioesterase 2 precursor |
| PRD7_HUMANMAJOR ISOFORM | Q9NQW5 | PR-domain zinc finger protein 7 |
| PSA7_HUMANISOFORM 4 | O14818 | Proteasome subunit alpha type 7 |
| PSD4_HUMANISOFORM RPN10E | P55036 | 26S proteasome non-ATPase regulatory subunit 4 |
| PSN1_HUMANISOFORM I-374 | P49768 | Presenilin 1 |
| PTPD_HUMANMAJOR ISOFORM | P23468 | Protein-tyrosine phosphatase delta precursor |
| R51D_HUMANISOFORM 2 | O94908 | DNA repair protein RAD51 homolog 4 |
| RBMS_HUMAN MAJOR ISOFORM | Q93062 | RNA-binding protein with multiple splicing |
| RED1_HUMANMAJOR ISOFORM | P78563 | Double-stranded RNA-specific editase 1 |
| RHD_HUMANMAJOR ISOFORM | Q9UQ21 | Blood group Rh |
| RHD_HUMANISOFORM 3 | Q9UQ21 | Blood group Rh |
| RYK_HUMANMAJOR ISOFORM | P34925 | Tyrosine-protein kinase RYK precursor |
| RYK_HUMANISOFORM 2 | P34925 | Tyrosine-protein kinase RYK precursor |
| SCA1_HUMANISOFORM 2 | O15126 | Secretory carrier-associated membrane protein 1 |
| SEN7_HUMANMAJOR ISOFORM | Q9BQF6 | Sentrin-specific protease 7 |
| SFR5_HUMANISOFORM SRP40-2 | Q13243 | Splicing factor arginine/serine-rich 5 |
| SHX2_HUMANMAJOR ISOFORM | O60902 | Short stature homeobox protein 2 |
| SNB2_HUMANISOFORM 2 | Q13425 | Beta-2-syntrophin |
| SNXD_HUMANISOFORM FORM 2 | Q9Y5W8 | Sorting nexin 13 |
| SON_HUMANISOFORM C | Q9UPY0 | SON protein |
| SON_HUMANISOFORM E | Q9UPY0 | SON protein |
| SUR5_HUMANISOFORM SURF5A | Q15528 | Surfeit locus protein 5 |
| T10B_HUMANMAJOR ISOFORM | O14763 | Tumor necrosis factor receptor superfamily member 10B precursor |
| T10B_HUMANISOFORM SHORT | O14763 | Tumor necrosis factor receptor superfamily member 10B precursor |
| TM31_HUMANISOFORM BETA | Q9BZY9 | Tripartite motif protein 31 |
| TNR6_HUMANISOFORM 2 | P25445 | Tumor necrosis factor receptor superfamily member 6 precursor |
| TNR6_HUMANISOFORM 3 | P25445 | Tumor necrosis factor receptor superfamily member 6 precursor |
| TNR6_HUMANISOFORM 4 | P25445 | Tumor necrosis factor receptor superfamily member 6 precursor |
| TNR6_HUMANISOFORM 5 | P25445 | Tumor necrosis factor receptor superfamily member 6 precursor |
| TPA_HUMANISOFORM SHORT | P00750 | Tissue-type plasminogen activator precursor |
| TPO_HUMANMAJOR ISOFORM | P40225 | Thrombopoietin precursor |
| TR12_HUMANISOFORM 12 | Q99831 | Tumor necrosis factor receptor superfamily member 12 precursor |
| TR12_HUMANISOFORM 3 | Q99831 | Tumor necrosis factor receptor superfamily member 12 precursor |
| TR12_HUMANISOFORM 4 | Q99831 | Tumor necrosis factor receptor superfamily member 12 precursor |
| TR12_HUMANISOFORM 5 | Q99831 | Tumor necrosis factor receptor superfamily member 12 precursor |
| TR12_HUMANISOFORM 6 | Q99831 | Tumor necrosis factor receptor superfamily member 12 precursor |
| TR12_HUMANISOFORM 7 | Q99831 | Tumor necrosis factor receptor superfamily member 12 precursor |
| U7I3_HUMANISOFORM 2 | Q9BYM8 | Ubiquitin conjugating enzyme 7 interacting protein 3 |
| U7I3_HUMANISOFORM 4 | Q9BYM8 | Ubiquitin conjugating enzyme 7 interacting protein 3 |
| USH3_HUMANISOFORM B | P58418 | Usher syndrome type 3 protein |
| WS14_HUMANISOFORM 5 | Q9NP71 | Williams-Beuren syndrome chromosome region 14 protein |
| XE7_HUMANISOFORM SHORT | Q02040 | B-lymphocyte antigen precursor |
| Z236_HUMANISOFORM A | Q9UL36 | Zinc finger protein 236 |
| ZAN_HUMANISOFORM 1 | Q9BXN9 | Zonadhesin precursor |
| ZAN_HUMANISOFORM 2 | Q9BXN9 | Zonadhesin precursor |
| ZAN_HUMANISOFORM 4 | Q9BXN9 | Zonadhesin precursor |
| ZAN_HUMANISOFORM 5. | Q9BXN9 | Zonadhesin precursor |

4. The method of claim 3 wherein the dataset of target putative protein isoform sequences comprises isoforms of Calpain-10, CLK1, CLK2, CLK3, and LARD/TNFRSF12.

5. A computer program product, comprising a computer usable medium having a computer readable program code embodied therein, said computer readable program code adapted to be executed to implement a method for systematically characterizing putative protein isoforms as apparent targets of nonsense-mediated decay (NMD) and for generating and outputting a list of said isoforms, the method comprising the following steps:
- identifying a dataset of target putative protein isoform sequences from a curated protein sequence database for characterization;
- identifying from an mRNA dataset corresponding mRNA sequences representing transcripts encoding the protein isoforms, wherein each of the transcripts comprises a termination codon and a final intron;
- determining corresponding gene intron-exon structures by mapping the mRNA sequences to corresponding genomic sequences;
- determining if the transcripts are apparent targets of NMD by comparing the position of the termination codon to the position of the final intron, wherein if the termination codon of the transcript is more than 50 nucleotides upstream of the final intron position, then the transcript is an apparent target of NMD; and
- outputting from the computer a list of said isoforms that are apparent targets of NMD, wherein the dataset of target putative protein isoform sequences comprises a subset of the isoforms of Table 1:

TABLE 1

Protein isoforms characterized as targets of NMD,

| ISOFORM NAME | ACCESSION | PROTEIN DESCRIPTION |
|---|---|---|
| 3BP2_HUMANISO FORM SHORT | P78314 | SH3 domain-binding protein 2 |
| 5H4_HUMANMAJOR ISOFORM | Q13639 | 5-hydroxytryptamine 4 receptor |
| A1A1_HUMANISO FORM SHORT | P05023 | Sodium/potassium-transporting ATPase alpha-1 chain precursor |
| ABCD_HUMANISO FORM 2 | Q9NSE7 | Putative ATP-binding cassette transporter C13 |
| ABCD_HUMANISO FORM 3 | Q9NSE7 | Putative ATP-binding cassette transporter C13 |
| AD11_HUMANISO FORM SHORT | O75078 | ADAM 11 precursor |
| AD12_HUMANMAJOR ISOFORM | O43184 | ADAM 12 precursor |
| AD22_HUMANISO FORM 2 | Q9POK1 | ADAM 22 precursor |
| AKP1_HUMANISO FORM 2 | Q92667 | A kinase anchor protein 1 mitochondrial precursor |
| ANPB_HUMANISO FORM SHORT | P20594 | Atrial natriuretic peptide receptor B precursor |
| AS13_HUMANMAJOR ISOFORM | Q8WXK3 | Ankyrin repeat and SOCS box containing protein 13 |
| AS13_HUMANISO FORM 2 | Q8WXK3 | Ankyrin repeat and SOCS box containing protein 13 |
| ATF3_HUMANISO FORM 2 | P18847 | Cyclic-AMP-dependent transcription factor ATF-3 |
| ATR_HUMANMAJOR ISOFORM | Q9H6X2 | Anthrax toxin receptor precursor |
| B3G7_HUMANISO FORM 2 | Q9NY97 | Beta-1 3-galactosyltransferase 7 |
| BC12_HUMANISO FORM 2 | Q9HB09 | Bcl-2 related proline-rich protein |
| BMP1_HUMANISO FORM BMP1-4 | P13497 | Bone morphogenetic protein 1 precursor |
| BMP1_HUMANISO FORM BMP1-5 | P13497 | Bone morphogenetic protein 1 precursor |
| BMP1_HUMANISO FORM BMP1-6 | P13497 | Bone morphogenetic protein 1 precursor |

TABLE 1-continued

Protein isoforms characterized as targets of NMD,

| ISOFORM NAME | ACCESSION | PROTEIN DESCRIPTION |
|---|---|---|
| C343_HUMANISO FORM 4 | Q9HB55 | Cytochrome P450 3A43 |
| CA34_HUMANMAJOR ISOFORM | Q01955 | Collagen alpha 3 |
| CA34_HUMANISO FORM 3 | Q01955 | Collagen alpha 3 |
| CAL0_HUMANISO FORM 2 | P01258 | Calcitonin precursor [Contains: Calcitonin; Katacalcin |
| CANA_HUMANISO FORM B | Q9HC93 | Calpain 10 |
| CANA_HUMANISO FORM D | Q9HC93 | Calpain 10 |
| CANA_HUMANISO FORM E | Q9HC93 | Calpain 10 |
| CANA_HUMANISO FORM F | Q9HC93 | Calpain 10 |
| CBS_HUMANMAJOR ISOFORM | P35520 | Cystathionine beta-synthase |
| CD38_HUMANISO FORM 2 | P28907 | ADP-ribosyl cyclase 1 |
| CD47_HUMANISO FORM OA3-305 | Q08722 | Leukocyte surface antigen CD47 precursor |
| CFLA_HUMANISO FORM 9 | O43618 | CASP8 and FADD-like apoptosis regulator precursor |
| CHRD_HUMANISO FORM 3 | Q9P0Z5 | Chordin precursor |
| CHRD_HUMANISO FORM 4 | Q9P0Z5 | Chordin precursor |
| CIQ2_HUMANISO FORM 3 | O43526 | Potassium voltage-gated channel subfamily KQT member 2 |
| CIW4_HUMANISO FORM 2 | Q9NYG8 | Potassium channel subfamily K member 4 |
| CLK1_HUMANISO FORM SHORT | P49759 | Protein kinase CLK1 |
| CLK2_HUMANISO FORM SHORT | P49760 | Protein kinase CLK2 |
| CLK3_HUMANISO FORM 2 | P49761 | Protein kinase CLK3 |
| CML1_HUMANMAJOR ISOFORM | Q99788 | Chemokine receptor-like 1 |
| COG4_HUMANISO FORM 2 | Q9H9E3 | Conserved oilgomeric Golgi complex component 4 |
| COLQ_HUMANISO FORM VII | Q9UP88 | Acetylcholinesterase collagenic tail peptide precursor |
| CPXM_HUMANISO FORM 2 | Q96SM3 | Potential carboxypeptidase X precursor |
| CRN1_HUMANISO FORM 4 | Q9NYD8 | Crooked neck-like protein 1 |
| CRN1_HUMANISO FORM 5 | Q9NYD8 | Crooked neck-like protein 1 |
| CT24_HUMANISO FORM 4 | Q9BUV8 | Protein C20orf24 |
| CTGF_HUMANMAJOR ISOFORM | P29279 | Connective tissue growth factor precursor |
| CU07_HUMANISO FORM B | P57077 | Protein C21orf7 |
| CU07_HUMANISO FORM C | P57077 | Protein C21orf7 |
| CU18_HUMANISO FORM B | Q9NVD3 | Protein C21orf18 |
| CU63_HUMANISO FORM B | P58658 | Protein C21orf63 precursor |
| CU80_HUMANISO FORM B | Q9Y2G5 | Protein C21orf80 |
| CYB5_HUMANISO FORM 2 | P00167 | Cytochrome b5 |
| DACA_HUMANISO FORM 2 | Q9BYJ9 | Dermatomyositis associated with cancer putative autoantigen-1 |
| DFFB_HUMANISO FORM BETA | O76075 | DNA fragmentation factor 40 kDa subunit |
| DFFB_HUMANISO FORM DELTA | O76075 | DNA fragmentation factor 40 kDa subunit |
| DFFB_HUMANISO | O76075 | DNA fragmentation factor 40 |

TABLE 1-continued

Protein isoforms characterized as targets of NMD.

| ISOFORM NAME | ACCESSION | PROTEIN DESCRIPTION |
|---|---|---|
| FORM GAMMA | | kDa subunit |
| DJB2_HUMANMAJOR ISOFORM | P25686 | DnaJ homolog subfamily B member 2 |
| DJB2_HUMANISO FORM 3 | P25686 | DnaJ homolog subfamily B member 2 |
| DONS_HUMANISO FORM 2 | Q9NYP3 | Downstream of son gene protein |
| DONS_HUMANIS OFORM 3 | Q9NYP3 | Downstream of son gene protein |
| DPP3_HUMANISO FORM 2 | Q9NY33 | Dipeptidyl-peptidase III |
| DSCA_HUMANISO FORM SHORT | O60469 | Down syndrome cell adhesion molecule precursor |
| DTNB_HUMANISO FORM 3 | O60941 | Dystrobrevin beta |
| EPA3_HUMANMAJOR ISOFORM | P29320 | Ephrin type-A receptor 3 precursor |
| ERAL_HUMANISO FORM HERA-B | O75616 | GTP-binding protein era homolog |
| ESR2_HUMANISO FORM 3 | Q9UHD3 | Estrogen receptor beta |
| F263_HUMANMAJOR ISOFORM | Q16875 | 6-phosphofructo-2-kinase/fructose-2 6-biphosphatase 3 |
| FAFY_HUMANISO FORM SHORT | O00507 | Probable ubiquitin carboxyl-terminal hydrolase FAF-Y |
| FCAR_HUMANISO FORM B-DELTA-S2 | P24071 | Immunoglobulin alpha Fc receptor precursor |
| FCE2_HUMANMAJOR ISOFORM | P06734 | Low affinity immunoglobulin epsilon FC receptor |
| FTCD_HUMANISO FORM E | O95954 | Formimidoyltransferase-cyclodeaminase |
| FUT8_HUMANISO FORM 2 | Q9BYC5 | Alpha-(1,6)-fucosyltransferase |
| FXM1_HUMANISO FORM 2 | Q08050 | Forkhead box protein M1 |
| G72_HUMANMAJOR ISOFORM | P59103 | Protein G72 |
| G72_HUMANISO FORM 2 | P59103 | Protein G72 |
| G8_HUMANMAJOR ISOFORM | Q9UBA6 | G8 protein |
| GBR1_HUMANISO FORM 1E | Q9UBS5 | Gamma-aminobutyric acid type B receptor subunit 1 precursor |
| GCFC_HUMANISO FORM D | Q9Y5B6 | GC-rich sequence DNA-binding factor homolog |
| GCP2_HUMANISO FORM 2 | Q9BSJ2 | Gamma-tubulin complex component 2 |
| GDNR_HUMANISO FORM 2 | P56159 | GDNF receptor alpha precursor |
| GLI2_HUMANMAJOR ISOFORM | P10070 | Zinc finger protein GLI2 |
| GLI2_HUMANISO FORM BETA | P10070 | Zinc finger protein GLI2 |
| GLI2_HUMANISO FORM DELTA | P10070 | Zinc finger protein GLI2 |
| GLI2_HUMANISO FORM GAMMA | P10070 | Zinc finger protein GLI2 |
| GLSK_HUMANISO FORM GAC | O94925 | Glutaminase kidney isoform mitochondrial precursor |
| GPT_HUMANMAJOR ISOFORM | Q9H3H5 | UDP-N-acetylglucosamine--dolichyl-phosphate N- |
| GRB2_HUMANMAJOR ISOFORM | P29354 | Growth factor receptor-bound protein 2 |
| HAIR_HUMANMAJOR ISOFORM | O43593 | Hairless protein |
| HAIR_HUMANISO FORM SHORT | O43593 | Hairless protein |
| HFE_HUMANMAJOR ISOFORM | Q9HC68 | Hereditary hemochromatosis protein precursor |
| I17S_HUMANISO FORM 2 | Q9NRM6 | Interleukin-17B receptor precursor |
| ICE2_HUMANISO FORM ICH-1S | P42575 | Caspase-2 precursor |
| ICE8_HUMANISO FORM 7 | Q9C0K4 | Caspase-8 precursor |
| ICEA_HUMANISO FORM B | Q92851 | Caspase-10 precursor |
| ICEA_HUMANISO FORM C | Q92851 | Caspase-10 precursor |
| ILF1_HUMANISO FORM 2 | Q01167 | Interleukin enhancer-binding factor 1 |
| IRF7_HUMANISO FORM C | Q92985 | Interferon regulatory factor 7 |
| IRL1_HUMANISO FORM C | Q01638 | Interleukin 1 receptor-like 1 precursor |
| ITP1_HUMANMAJOR ISOFORM | O14713 | Integrin beta-1 binding protein 1 |
| ITP1_HUMANISO FORM 2 | O14713 | Integrin beta-1 binding protein 1 |
| KC11_HUMANIS OFORM 1S | Q9HCP0 | Casein kinase I gamma 1 isoform |
| KLK2_HUMANIS OFORM 3 | P20151 | Glandular kallikrein 2 precursor |
| KLKF_HUMANISO FORM 2 | Q9H2R5 | Kallikrein 15 precursor |
| LEF1_HUMANISO FORM B | Q9UJU2 | Lymphoid enhancer binding factor 1 |
| LFA3_HUMANISO FORM SHORT | P19256 | Lymphocyte function-associated antigen 3 precursor |
| LIK1_HUMANISO FORM 3 | P53667 | LIM domain kinase 1 |
| LSHR_HUMANMAJOR ISOFORM | P22888 | Lutropin-choriogonadotropic hormone receptor precursor |
| LYST_HUMANMAJOR ISOFORM | Q99698 | Lysosomal trafficking regulator |
| M2A2_HUMANISO FORM SHORT | P49641 | Alpha-mannosidase IIx |
| MADI_HUMANISO FORM 2 | O95405 | Mothers against decapentaplegic homolog interacting protein |
| MAP2_HUMAN MAJOR ISOFORM | P11137 | Microtubule-associated protein 2 |
| MAP2_HUMANI SOFORM MAP2C | P11137 | Microtubule-associated protein 2 |
| MAP4_HUMANI SOFORM 2 | P27816 | Microtubule-associated protein 4 |
| MAX_HUMANISO FORM 3 | P25912 | Max protein |
| MK11_HUMANISO FORM BETA-2 | Q15759 | Mitogen-activated protein kinase 11 |
| MLH3_HUMANISO FORM 2 | Q9UHC1 | DNA mismatch repair protein Mlh3 |
| MRP3_HUMANISO FORM 3A | O15438 | Canalicular multispecific organic anion transporter 2 |
| MRP3_HUMANISO FORM 3B | O15438 | Canalicular multispecific organic anion transporter 2 |
| MSRE_HUMANISO FORM II | P21757 | Macrophage scavenger receptor types I and II |
| MTF2_HUMANMAJOR ISOFORM | Q9Y483 | Metal-response element-binding transcription factor 2 |
| NK31_HUMANMAJOR ISOFORM | Q99801 | Homeobox protein Nkx-31 |
| NXF5_HUMANMAJOR ISOFORM | Q9H1B4 | Nuclear RNA export factor 5 |
| NXFS_HUMANISO FORM B | Q9H1B4 | Nuclear RNA export factor 5 |
| NXFS_HUMANISO FORM C | Q9H1B4 | Nuclear RNA export factor 5 |
| NXF5_HUMANISO FORM D | Q9H1B4 | Nuclear RNA export factor 5 |
| NXFS_HUMANISO FORM E | Q9H1B4 | Nuclear RNA export factor 5 |
| PHMX_HUMANISO FORM 4 | Q96QS1 | Phemx protein |

TABLE 1-continued

Protein isoforms characterized as targets of NMD.

| ISOFORM NAME | ACCESSION | PROTEIN DESCRIPTION |
|---|---|---|
| PHMX_HUMANISOFORM 5 | Q96QS1 | Phemx protein |
| PML_HUMANISOFORM PML-3B | P29590 | Probable transcription factor PML |
| PPE1_HUMANISOFORM 2 | O14829 | Serine/threonine protein phosphatase with EF-hands-1 |
| PPT2_HUMANISOFORM 2 | Q9UMR5 | Palmitoyl-protein thioesterase 2 precursor |
| PRD7_HUMANMAJOR ISOFORM | Q9NQW5 | PR-domain zinc finger protein 7 |
| PSA7_HUMANISOFORM 4 | O14818 | Proteasome subunit alpha type 7 |
| PSD4_HUMANISOFORM RPN10E | P55036 | 26S proteasome non-ATPase regulatory subunit 4 |
| PSN1_HUMANISOFORM I-374 | P49768 | Presenilin 1 |
| PTPD_HUMANMAJOR ISOFORM | P23468 | Protein-tyrosine phosphatase delta precursor |
| R51D_HUMANISOFORM 2 | O94908 | DNA repair protein RAD51 homolog 4 |
| RBMS_HUMAN MAJOR ISOFORM | Q93062 | RNA-binding protein with multiple splicing |
| RED1_HUMANMAJOR ISOFORM | P78563 | Double-stranded RNA-specific editase 1 |
| RHD_HUMANMAJOR ISOFORM | Q9UQ21 | Blood group Rh |
| RHD_HUMANISOFORM 3 | Q9UQ21 | Blood group Rh |
| RYK_HUMANMAJOR ISOFORM | P34925 | Tyrosine-protein kinase RYK precursor |
| RYK_HUMANISOFORM 2 | P34925 | Tyrosine-protein kinase RYK precursor |
| SCA1_HUMANISOFORM 2 | O15126 | Secretory carrier-associated membrane protein 1 |
| SEN7_HUMANMAJOR ISOFORM | Q9BQF6 | Sentrin-specific protease 7 |
| SFR5_HUMANISOFORM SRP40-2 | Q13243 | Splicing factor arginine/serine-rich 5 |
| SHX2_HUMANMAJOR ISOFORM | O60902 | Short stature homeobox protein 2 |
| SNB2_HUMANISOFORM 2 | Q13425 | Beta-2-syntrophin |
| SNXD_HUMANISOFORM 2 | Q9Y5W8 | Sorting nexin 13 |
| SON_HUMANISOFORM C | Q9UPY0 | SON protein |
| SON_HUMANISOFORM E | Q9UPY0 | SON protein |
| SUR5_HUMANISOFORM SURF5A | Q15528 | Surfeit locus protein 5 |
| T10B_HUMANMAJOR ISOFORM | O14763 | Tumor necrosis factor receptor superfamily member 10B precursor |
| T10B_HUMANISOFORM SHORT | O14763 | Tumor necrosis factor receptor superfamily member 10B precursor |
| TM31_HUMANISOFORM BETA | Q9BZY9 | Tripartite motif protein 31 |
| TNR6_HUMANISOFORM 2 | P25445 | Tumor necrosis factor receptor superfamily member 6 precursor |
| TNR6_HUMANISOFORM 3 | P25445 | Tumor necrosis factor receptor superfamily member 6 precursor |
| TNR6_HUMANISOFORM 4 | P25445 | Tumor necrosis factor receptor superfamily member 6 precursor |
| TNR6_HUMANISOFORM 5 | P25445 | Tumor necrosis factor receptor superfamily member 6 precursor |
| TPA_HUMANISOFORM SHORT | P00750 | Tissue-type plasminogen activator precursor |
| TPO_HUMANMAJOR ISOFORM | P40225 | Thrombopoietin precursor |
| TR12_HUMANISOFORM 12 | Q99831 | Tumor necrosis factor receptor superfamily member 12 precursor |
| TR12_HUMANISOFORM 3 | Q99831 | Tumor necrosis factor receptor superfamily member 12 precursor |
| TR12_HUMANISOFORM 4 | Q99831 | Tumor necrosis factor receptor superfamily member 12 precursor |
| TR12_HUMANISOFORM 5 | Q99831 | Tumor necrosis factor receptor superfamily member 12 precursor |
| TR12_HUMANISOFORM 6 | Q99831 | Tumor necrosis factor receptor superfamily member 12 precursor |
| TR12_HUMANISOFORM 7 | Q99831 | Tumor necrosis factor receptor superfamily member 12 precursor |
| U7I3_HUMANISOFORM 2 | Q9BYM8 | Ubiquitin conjugating enzyme 7 interacting protein 3 |
| U7I3_HUMANISOFORM 4 | Q9BYM8 | Ubiquitin conjugating enzyme 7 interacting protein 3 |
| USH3_HUMANISOFORM B | P58418 | Usher syndrome type 3 protein |
| WS14_HUMANISOFORM 5 | Q9NP71 | Williams-Beuren syndrome chromosome region 14 protein |
| XE7_HUMANISOFORM SHORT | Q02040 | B-lymphocyte antigen precursor |
| Z236_HUMANISOFORM A | Q9UL36 | Zinc finger protein 236 |
| ZAN_HUMANISOFORM 1 | Q9BXN9 | Zonadhesin precursor |
| ZAN_HUMANISOFORM 2 | Q9BXN9 | Zonadhesin precursor |
| ZAN_HUMANISOFORM 4 | Q9BXN9 | Zonadhesin precursor |
| ZAN_HUMANISOFORM 5. | Q9BXN9 | Zonadhesin precursor |

6. The product of claim 5 wherein the dataset of target putative protein isoform sequences comprises isoforms of Calpain-10, CLK1, CLK2, CLK3, and LARD/TNFRSF12.

7. A computer program product, comprising a computer usable medium having a computer readable program code embodied therein, said computer readable program code adapted to be executed to implement a method for systematically characterizing putative protein isoforms as apparent targets of nonsense-mediated decay (NMD) and for generating and outputting a list of said isoforms, the method comprising the following steps:

identifying a dataset of target putative protein isoform sequences from a curated protein sequence database for characterization;

identifying corresponding gene intron-exon structures by mapping corresponding mRNA sequences of an mRNA sequence dataset to genomic sequences of a genomic DNA sequence dataset;

screening the isoform dataset for a subset of isoforms encoded by transcripts comprising alternate splices which introduce a stop codon more than 50 nucleotides upstream of the final exon-exon splice junction; and classifying the subset isoforms as being encoded by transcripts comprising premature stop codons and as targets of NMD; and outputting from the computer a list of said isoforms that are apparent targets of NMD, wherein the dataset of target putative protein isoform sequences comprises a subset of the isoforms of Table 1:

TABLE 1

Protein isoforms characterized as targets of NMD.

| ISOFORM NAME | ACCESSION | PROTEIN DESCRIPTION |
|---|---|---|
| 3BP2_HUMANISOFORM SHORT | P78314 | SH3 domain-binding protein 2 |
| 5H4_HUMANMAJOR ISOFORM | Q13639 | 5-hydroxytryptamine 4 receptor |
| A1A1_HUMANISOFORM SHORT | P05023 | Sodium/potassium-transporting ATPase alpha-1 chain precursor |
| ABCD_HUMANISOFORM 2 | Q9NSE7 | Putative ATP-binding cassette transporter C13 |
| ABCD_HUMANISOFORM 3 | Q9NSE7 | Putative ATP-binding cassette transporter C13 |
| AD11_HUMANISOFORM SHORT | O75078 | ADAM 11 precursor |
| AD12_HUMANMAJOR ISOFORM | O43184 | ADAM 12 precursor |
| AD22_HUMANISOFORM 2 | Q9POK1 | ADAM 22 precursor |
| AKP1_HUMANISOFORM 2 | Q92667 | A kinase anchor protein 1 mitochondrial precursor |
| ANPB_HUMANISOFORM SHORT | P20594 | Atrial natriuretic peptide receptor B precursor |
| AS13_HUMANMAJOR ISOFORM | Q8WXK3 | Ankyrin repeat and SOCS box containing protein 13 |
| AS13_HUMANISOFORM 2 | Q8WXK3 | Ankyrin repeat and SOCS box containing protein 13 |
| ATF3_HUMANISOFORM 2 | P18847 | Cyclic-AMP-dependent transcription factor ATF-3 |
| ATR_HUMANMAJOR ISOFORM | Q9H6X2 | Anthrax toxin receptor precursor |
| B3G7_HUMANISOFORM 2 | Q9NY97 | Beta-1 3-galactosyltransferase 7 |
| BC12_HUMANISOFORM 2 | Q9HB09 | Bcl-2 related proline-rich protein |
| BMP1_HUMANISOFORM BMP1-4 | P13497 | Bone morphogenetic protein 1 precursor |
| BMP1_HUMANISOFORM BMP1-5 | P13497 | Bone morphogenetic protein 1 precursor |
| BMP1_HUMANISOFORM BMP1-6 | P13497 | Bone morphogenetic protein 1 precursor |
| C343_HUMANISOFORM 4 | Q9HB55 | Cytochrome P450 3A43 |
| CA34_HUMANMAJOR ISOFORM | Q01955 | Collagen alpha 3 |
| CA34_HUMANISOFORM 3 | Q01955 | Collagen alpha 3 |
| CAL0_HUMANISOFORM 2 | P01258 | Calcitonin precursor [Contains: Calcitonin; Katacalcin] |
| CANA_HUMANISOFORM B | Q9HC93 | Calpain 10 |
| CANA_HUMANISOFORM D | Q9HC93 | Calpain 10 |
| CANA_HUMANISOFORM E | Q9HC93 | Calpain 10 |
| CANA_HUMANISOFORM F | Q9HC93 | Calpain 10 |
| CBS_HUMANMAJOR ISOFORM | P35520 | Cystathionine beta-synthase |
| CD38_HUMANISOFORM 2 | P28907 | ADP-ribosyl cyclase 1 |
| CD47_HUMANISOFORM OA3-305 | Q08722 | Leukocyte surface antigen CD47 precursor |
| CFLA_HUMANISOFORM 9 | O43618 | CASP8 and FADD-like apoptosis regulator precursor |
| CHRD_HUMANISOFORM 3 | Q9P0Z5 | Chordin precursor |
| CHRD_HUMANISOFORM 4 | Q9P0Z5 | Chordin precursor |
| CIQ2_HUMANISOFORM 3 | O43526 | Potassium voltage-gated channel subfamily KQT member 2 |
| CIW4_HUMANISOFORM 2 | Q9NYG8 | Potassium channel subfamily K member 4 |
| CLK1_HUMANISOFORM SHORT | P49759 | Protein kinase CLK1 |
| CLK2_HUMANISOFORM SHORT | P49760 | Protein kinase CLK2 |
| CLK3_HUMANISOFORM 2 | P49761 | Protein kinase CLK3 |
| CML1_HUMANMAJOR ISOFORM | Q99788 | Chemokine receptor-like 1 |
| COG4_HUMANISOFORM 2 | Q9H9E3 | Conserved oilgomeric Golgi complex component 4 |
| COLQ_HUMANISOFORM VII | Q9UP88 | Acetylcholinesterase collagenic tail peptide precursor |
| CPXM_HUMANISOFORM 2 | Q96SM3 | Potential carboxypeptidase X precursor |
| CRN1_HUMANISOFORM 4 | Q9NYD8 | Crooked neck-like protein 1 |
| CRN1_HUMANISOFORM 5 | Q9NYD8 | Crooked neck-like protein 1 |
| CT24_HUMANISOFORM 4 | Q9BUV8 | Protein C20orf24 |
| CTGF_HUMANMAJOR ISOFORM | P29279 | Connective tissue growth factor precursor |
| CU07_HUMANISOFORM B | P57077 | Protein C21orf7 |
| CU07_HUMANISOFORM C | P57077 | Protein C21orf7 |
| CU18_HUMANISOFORM B | Q9NVD3 | Protein C21orf18 |
| CU63_HUMANISOFORM B | P58658 | Protein C21orf63 precursor |
| CU80_HUMANISOFORM B | Q9Y2G5 | Protein C21orf80 |
| CYB5_HUMANISOFORM 2 | P00167 | Cytochrome b5 |
| DACA_HUMANISOFORM 2 | Q9BYJ9 | Dermatomyositis associated with cancer putative autoantigen-1 |
| DFFB_HUMANISOFORM BETA | O76075 | DNA fragmentation factor 40 kDa subunit |
| DFFB_HUMANISOFORM DELTA | O76075 | DNA fragmentation factor 40 kDa subunit |
| DFFB_HUMANISOFORM GAMMA | O76075 | DNA fragmentation factor 40 kDa subunit |
| DJB2_HUMANMAJOR ISOFORM | P25686 | DnaJ homolog subfamily B member 2 |
| DJB2_HUMANISOFORM 3 | P25686 | DnaJ homolog subfamily B member 2 |
| DONS_HUMANISOFORM 2 | Q9NYP3 | Downstream of son gene protein |
| DONS_HUMANISOFORM 3 | Q9NYP3 | Downstream of son gene protein |
| DPP3_HUMANISOFORM 2 | Q9NY33 | Dipeptidyl-peptidase III |
| DSCA_HUMANISOFORM SHORT | O60469 | Down syndrome cell adhesion molecule precursor |
| DTNB_HUMANISOFORM 3 | O60941 | Dystrobrevin beta |
| EPA3_HUMANMAJOR ISOFORM | P29320 | Ephrin type-A receptor 3 precursor |
| ERAL_HUMANISOFORM HERA-B | O75616 | GTP-binding protein era homolog |
| ESR2_HUMANISOFORM 3 | Q9UHD3 | Estrogen receptor beta |
| F263_HUMANMAJOR ISOFORM | Q16875 | 6-phosphofructo-2-kinase/fructose-2 6-biphosphatase 3 |
| FAFY_HUMANISOFORM SHORT | O00507 | Probable ubiquitin carboxyl-terminal hydrolase FAF-Y |
| FCAR_HUMANISOFORM B-DELTA-S2 | P24071 | Immunoglobulin alpha Fc receptor precursor |
| FCE2_HUMANMAJOR ISOFORM | P06734 | Low affinity immunoglobulin epsilon FC receptor |
| FTCD_HUMANISOFORM E | O95954 | Formimidoyltransferase-cyclodeaminase |
| FUT8_HUMANISOFORM 2 | Q9BYC5 | Alpha-(1,6)-fucosyltransferase |
| FXM1_HUMANISOFORM 2 | Q08050 | Forkhead box protein M1 |

TABLE 1-continued

Protein isoforms characterized as targets of NMD.

| ISOFORM NAME | ACCESSION | PROTEIN DESCRIPTION |
|---|---|---|
| G72_HUMANMAJOR ISOFORM | P59103 | Protein G72 |
| G72_HUMANISO FORM 2 | P59103 | Protein G72 |
| G8_HUMANMAJOR ISOFORM | Q9UBA6 | G8 protein |
| GBR1_HUMANISO FORM 1E | Q9UBS5 | Gamma-aminobutyric acid type B receptor subunit 1 precursor |
| GCFC_HUMANISO FORM D | Q9Y5B6 | GC-rich sequence DNA-binding factor homolog |
| GCP2_HUMANISO FORM 2 | Q9BSJ2 | Gamma-tubulin complex component 2 |
| GDNR_HUMANISO FORM 2 | P56159 | GDNF receptor alpha precursor |
| GLI2_HUMANMAJOR ISOFORM | P10070 | Zinc finger protein GLI2 |
| GLI2_HUMANISO FORM BETA | P10070 | Zinc finger protein GLI2 |
| GLI2_HUMANISO FORM DELTA | P10070 | Zinc finger protein GLI2 |
| GLI2_HUMANISO FORM GAMMA | P10070 | Zinc finger protein GLI2 |
| GLSK_HUMANISO FORM GAC | O94925 | Glutaminase kidney isoform mitochondrial precursor |
| GPT_HUMANMAJOR ISOFORM | Q9H3H5 | UDP-N-acetylglucosamine--dolichyl-phosphate N- |
| GRB2_HUMANMAJOR ISOFORM | P29354 | Growth factor receptor-bound protein 2 |
| HAIR_HUMANMAJOR ISOFORM | O43593 | Hairless protein |
| HAIR_HUMANISO FORM SHORT | O43593 | Hairless protein |
| HFE_HUMANMAJOR ISOFORM | Q9HC68 | Hereditary hemochromatosis protein precursor |
| I17S_HUMANISO FORM 2 | Q9NRM6 | Interleukin-17B receptor precursor |
| ICE2_HUMANISO FORM ICH-1S | P42575 | Caspase-2 precursor |
| ICE8_HUMANISO FORM 7 | Q9C0K4 | Caspase-8 precursor |
| ICEA_HUMANISO FORM B | Q92851 | Caspase-10 precursor |
| ICEA_HUMANISO FORM C | Q92851 | Caspase-10 precursor |
| ILF1_HUMANISO FORM 2 | Q01167 | Interleukin enhancer-binding factor 1 |
| IRF7_HUMANISO FORM C | Q92985 | Interferon regulatory factor 7 |
| IRL1_HUMANISO FORM C | Q01638 | Interleukin 1 receptor-like 1 precursor |
| ITP1_HUMANMAJOR ISOFORM | O14713 | Integrin beta-1 binding protein 1 |
| ITP1_HUMANISO FORM 2 | O14713 | Integrin beta-1 binding protein 1 |
| KC11_HUMANIS OFORM 1S | Q9HCP0 | Casein kinase I gamma 1 isoform |
| KLK2_HUMANIS OFORM 3 | P20151 | Glandular kallikrein 2 precursor |
| KLKF_HUMANISO FORM 2 | Q9H2R5 | Kallikrein 15 precursor |
| LEF1_HUMANISO FORM B | Q9UJU2 | Lymphoid enhancer binding factor 1 |
| LFA3_HUMANISO FORM SHORT | P19256 | Lymphocyte function-associated antigen 3 precursor |
| LIK1_HUMANISO FORM 3 | P53667 | LIM domain kinase 1 |
| LSHR_HUMANMAJOR ISOFORM | P22888 | Lutropin-choriogonadotropic hormone receptor precursor |
| LYST_HUMANMAJOR ISOFORM | Q99698 | Lysosomal trafficking regulator |
| M2A2_HUMANISO FORM SHORT | P49641 | Alpha-mannosidase IIx |
| MADI_HUMANISO FORM 2 | O95405 | Mothers against decapentaplegic homolog interacting protein |
| MAP2_HUMAN MAJOR ISOFORM | P11137 | Microtubule-associated protein 2 |
| MAP2_HUMANI SOFORM MAP2C | P11137 | Microtubule-associated protein 2 |
| MAP4_HUMANI SOFORM 2 | P27816 | Microtubule-associated protein 4 |
| MAX_HUMANISO FORM 3 | P25912 | Max protein |
| MK11_HUMANISO FORM BETA-2 | Q15759 | Mitogen-activated protein kinase 11 |
| MLH3_HUMANISO FORM 2 | Q9UHC1 | DNA mismatch repair protein Mlh3 |
| MRP3_HUMANISO FORM 3A | O15438 | Canalicular multispecific organic anion transporter 2 |
| MRP3_HUMANISO FORM 3B | O15438 | Canalicular multispecific organic anion transporter 2 |
| MSRE_HUMANISO FORM II | P21757 | Macrophage scavenger receptor types I and II |
| MTF2_HUMANMAJOR ISOFORM | Q9Y483 | Metal-response element-binding transcription factor 2 |
| NK31_HUMANMAJOR ISOFORM | Q99801 | Homeobox protein Nkx-31 |
| NXF5_HUMANMAJOR ISOFORM | Q9H1B4 | Nuclear RNA export factor 5 |
| NXFS_HUMANISO FORM B | Q9H1B4 | Nuclear RNA export factor 5 |
| NXFS_HUMANISO FORM C | Q9H1B4 | Nuclear RNA export factor 5 |
| NXF5_HUMANISO FORM D | Q9H1B4 | Nuclear RNA export factor 5 |
| NXFS_HUMANISO FORM E | Q9H1B4 | Nuclear RNA export factor 5 |
| PHMX_HUMANISO FORM 4 | Q96QS1 | Phemx protein |
| PHMX_HUMANISO FORM 5 | Q96QS1 | Phemx protein |
| PML_HUMANISO FORM PML-3B | P29590 | Probable transcription factor PML |
| PPE1_HUMANISO FORM 2 | O14829 | Serine/threonine protein phosphatase with EF-hands-1 |
| PPT2_HUMANISO FORM 2 | Q9UMR5 | Palmitoyl-protein thioesterase 2 precursor |
| PRD7_HUMANMAJOR ISOFORM | Q9NQW5 | PR-domain zinc finger protein 7 |
| PSA7_HUMANISO FORM 4 | O14818 | Proteasome subunit alpha type 7 |
| PSD4_HUMANISO FORM RPN10E | P55036 | 26S proteasome non-ATPase regulatory subunit 4 |
| PSN1_HUMANISO FORM I-374 | P49768 | Presenilin 1 |
| PTPD_HUMANMAJOR ISOFORM | P23468 | Protein-tyrosine phosphatase delta precursor |
| R51D_HUMANISO FORM 2 | O94908 | DNA repair protein RAD51 homolog 4 |
| RBMS_HUMAN MAJOR ISOFORM | Q93062 | RNA-binding protein with multiple splicing |
| RED1_HUMANMAJOR ISOFORM | P78563 | Double-stranded RNA-specific editase 1 |
| RHD_HUMANMAJOR ISOFORM | Q9UQ21 | Blood group Rh |
| RHD_HUMANISO FORM 3 | Q9UQ21 | Blood group Rh |
| RYK_HUMANMAJOR ISOFORM | P34925 | Tyrosine-protein kinase RYK precursor |
| RYK_HUMANIS OFORM 2 | P34925 | Tyrosine-protein kinase RYK precursor |
| SCA1_HUMANISO FORM 2 | O15126 | Secretory carrier-associated membrane protein 1 |
| SEN7_HUMANMAJOR ISOFORM | Q9BQF6 | Sentrin-specific protease 7 |

TABLE 1-continued

Protein isoforms characterized as targets of NMD.

| ISOFORM NAME | ACCESSION | PROTEIN DESCRIPTION |
|---|---|---|
| SFR5_HUMANISOFORM SRP40-2 | Q13243 | Splicing factor arginine/serine-rich 5 |
| SHX2_HUMANMAJOR ISOFORM | O60902 | Short stature homeobox protein 2 |
| SNB2 HUMANISO FORM 2 | Q13425 | Beta-2-syntrophin |
| SNXD_HUMANISO FORM 2 | Q9Y5W8 | Sorting nexin 13 |
| SON_HUMANISO FORM C | Q9UPY0 | SON protein |
| SON_HUMANISO FORM E | Q9UPY0 | SON protein |
| SUR5_HUMANISO FORM SURF5A | Q15528 | Surfeit locus protein 5 |
| T10B_HUMANMAJOR ISOFORM | O14763 | Tumor necrosis factor receptor superfamily member 10B precursor |
| T10B HUMANISO FORM SHORT | O14763 | Tumor necrosis factor receptor superfamily member 10B precursor |
| TM31_HUMANISO FORM BETA | Q9BZY9 | Tripartite motif protein 31 |
| TNR6_HUMANISO FORM 2 | P25445 | Tumor necrosis factor receptor superfamily member 6 precursor |
| TNR6_HUMANISO FORM 3 | P25445 | Tumor necrosis factor receptor superfamily member 6 precursor |
| TNR6_HUMANISO FORM 4 | P25445 | Tumor necrosis factor receptor superfamily member 6 precursor |
| TNR6_HUMANISO FORM 5 | P25445 | Tumor necrosis factor receptor superfamily member 6 precursor |
| TPA_HUMANISO FORM SHORT | P00750 | Tissue-type plasminogen activator precursor |
| TPO HUMANMAJOR ISOFORM | P40225 | Thrombopoietin precursor |
| TR12_HUMANISO FORM 12 | Q99831 | Tumor necrosis factor receptor superfamily member 12 precursor |
| TR12_HUMANISO FORM 3 | Q99831 | Tumor necrosis factor receptor superfamily member 12 precursor |
| TR12_HUMANISO FORM 4 | Q99831 | Tumor necrosis factor receptor superfamily member 12 precursor |
| TR12_HUMANISO FORM 5 | Q99831 | Tumor necrosis factor receptor superfamily member 12 precursor |
| TR12_HUMANISO FORM 6 | Q99831 | Tumor necrosis factor receptor superfamily member 12 precursor |
| TR12_HUMANISO FORM 7 | Q99831 | Tumor necrosis factor receptor superfamily member 12 precursor |
| U7I3_HUMANISO FORM 2 | Q9BYM8 | Ubiquitin conjugating enzyme 7 interacting protein 3 |
| U7I3_HUMANISO FORM 4 | Q9BYM8 | Ubiquitin conjugating enzyme 7 interacting protein 3 |
| USH3_HUMANISO FORM B | P58418 | Usher syndrome type 3 protein |
| WS14_HUMANISO FORM 5 | Q9NP71 | Williams-Beuren syndrome chromosome region 14 protein |
| XE7_HUMANISO FORM SHORT | Q02040 | B-lymphocyte antigen precursor |
| Z236_HUMANISO FORM A | Q9UL36 | Zinc finger protein 236 |
| ZAN_HUMANISO FORM 1 | Q9BXN9 | Zonadhesin precursor |
| ZAN_HUMANISO FORM 2 | Q9BXN9 | Zonadhesin precursor |
| ZAN_HUMANISO FORM 4 | Q9BXN9 | Zonadhesin precursor |
| ZAN_HUMANISO FORM 5. | Q9BXN9 | Zonadhesin precursor |

8. The product of claim 7 wherein the dataset of target putative protein isoform sequences comprises isoforms of Calpain-10, CLK1, CLK2, CLK3, and LARD/TNFRSF12.

\* \* \* \* \*